United States Patent
Feinberg et al.

(10) Patent No.: US 9,500,658 B2
(45) Date of Patent: Nov. 22, 2016

(54) KRUPPEL-LIKE FACTOR 10 (KLF10) AS A BIOMARKER OF ENDOTHELIAL PROGENITOR CELL DYSFUNCTION

(75) Inventors: Mark W. Feinberg, Newton, MA (US); Akm Khyrul Wara, West Roxbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/003,852

(22) PCT Filed: Mar. 9, 2012

(86) PCT No.: PCT/US2012/028434
§ 371 (c)(1),
(2), (4) Date: Feb. 18, 2014

(87) PCT Pub. No.: WO2012/122453
PCT Pub. Date: Sep. 13, 2012

(65) Prior Publication Data
US 2014/0162947 A1    Jun. 12, 2014

Related U.S. Application Data

(60) Provisional application No. 61/450,944, filed on Mar. 9, 2011.

(51) Int. Cl.
| | | |
|---|---|---|
| A61K 38/18 | (2006.01) | |
| G01N 33/00 | (2006.01) | |
| C12Q 1/68 | (2006.01) | |
| G01N 33/68 | (2006.01) | |

(52) U.S. Cl.
CPC ...... *G01N 33/6872* (2013.01); *G01N 33/6893* (2013.01); *G01N 2333/4703* (2013.01); *G01N 2800/32* (2013.01); *G01N 2800/50* (2013.01)

(58) Field of Classification Search
CPC ............. G01N 2800/52; G01N 33/57434; G01N 33/6893; G01N 33/6896; G01N 33/505; G01N 33/574; G01N 33/68; G01N 33/6872; G01N 33/74; G01N 1/2813; G01N 1/34; G01N 2333/70585; G01N 2333/726; G01N 2333/912; G01N 2500/04; G01N 2500/10; G01N 2500/20; G01N 2800/102; G01N 2800/20; G01N 2800/202; G01N 2800/205; G01N 2800/2835; G01N 2800/304; G01N 2800/50; G01N 2800/56; G01N 33/5008; G01N 33/5044; G01N 33/57407; G01N 33/57415; G01N 33/57423; G01N 33/57484; G01N 33/6803; G01N 33/6854; G01N 33/6881

See application file for complete search history.

(56) References Cited

U.S. PATENT DOCUMENTS 5,675,062 A    10/1997    Haber et al.
2010/0092958 A1*    4/2010    Simons et al. ............. 435/6

OTHER PUBLICATIONS

Vasan. Biomarkers of Cardiovascular Disease: Molecular Basis and Practical Considerations. Circulation. 2006; 113:2335-2362.*
Kroese et al. Genetic tests and their evaluation: Can we answer the key questions?Genetics in Medicine 6(6): 475-480, 2004.*
Wood. New England Journal of Medicine, 344(21), 2001.*
Rahman et al. Int J Diabetes Dev Ctries. Jul.-Aug. 2009; 29(3): 110-117.*
Spahn et al. British Journal of Anaesthesia. 2006; 96(6): 675-677.*
Alder et al., "Kruppel-like factor 4 is essential for inflammatory monocyte differentiation in vivo," J. Immunol., 180:5645-5652 (2008).
Basu et al., "Transforming growth factor-{beta}1 modulates responses of CD34+ cord blood cells to stromal cell-derived factor-1/CXCL12," Blood, 106:485-493 (2005).
Bieker et al., "Krüppel-like factors: three fingers in many pies," Journal of Biological Chemistry, 276:34355-34358 (2001).
Billingham, "Graft coronary disease: the lesions and the patients," Transplant Proc., 21:3665-66 (1989).
Burt et al., "Clinical applications of blood-derived and marrow-derived stem cells for nonmalignant diseases," JAMA, 299:925-936 (2008).
Cao et al., "Kruppel-like factor KLF10 targets transforming growth factor-beta1 to regulate CD4(+)CD25(−) T cells and T regulatory cells," J. Biol. Chem., 284:24914-24924 (2009).
Cao et al., "Role of Kruppel-like factors in leukocyte development, function, and disease," Blood, 116(22):4404-14 (2010).
Capron et al., "A major role of TGF-beta1 in the homing capacities of murine hematopoietic stem cell/progenitors," Blood, 116:1244-1253 (2010).
Coppola et al., "Peripheral artery disease: potential role of ACE-inhibitor therapy," Vasc. Health Risk Manag., 4(6):1179-1187 (2008).
Devanesan et al., "Endothelial progenitor cells as a therapeutic option in peripheral arterial disease," Eur. J. Vasc. Endovasc. Surg., 38:475-481 (2009).
Fadini et al., "Number and Function of Endothelial Progenitor Cells as a Marker of Severity for Diabetic Vasculopathy," Arterioscler. Thromb. Vasc. Biol., 26:2140-2146 (2006).
Feinberg et al., "An emerging role for Krüppel-like factors in vascular biology," Trends Cardiovasc. Med., 14:241-246 (2004).
Feinberg et al., "Role of transforming growth factor-beta1/Smads in regulating vascular inflammation and atherogenesis," Panminerva Medica., 47:169-186 (2005).
Feinberg et al., "The Kruppel-like factor KLF4 is a critical regulator of monocyte differentiation," EMBO Journal, 26:4138-4148 (2007).
Felker et al., "A standardized definition of ischemic cardiomyopathy for use in clinical research," J. Am. Coll. Cardiol., 39(2):210 (2002).

(Continued)

*Primary Examiner* — Vanessa L Ford
*Assistant Examiner* — Sandra Dillahunt
(74) *Attorney, Agent, or Firm* — Fish & Richardson P.C.

(57) ABSTRACT

The use of Kruppel-like Factor (KLF10) as a diagnostic and prognostic tool for peripheral artery disease and other disease conditions associated with reduced angiogenesis or endothelial progenitor cell dysfunction such as diabetes and stent thrombosis.

14 Claims, 16 Drawing Sheets

(56) References Cited

OTHER PUBLICATIONS

Fowler, Michael J., "Microvascular and Macrovascular Complications of Diabetes," Clinical Diabetes, 26(2):77-82 (2008).
Franitza et al., "TGF-beta1 enhances SDF-1alpha-induced chemotaxis and homing of naive T cells by up-regulating CXCR4 expression and downstream cytoskeletal effector molecules," Eur. J. Immunol., 32:193-202 (2002).
Frontelo et al., "Novel role for EKLF in megakaryocyte lineage commitment," Blood 110:3871-3880 (2007).
Ghosh et al., "Antagonistic regulation of type I collagen gene expression by interferon-gamma and transforming growth factor-beta. Integration at the level of p300/CBP transcriptional coactivators," J. Biol. Chem., 276:11041-11048 (2001).
Grove and Kristensen, "Stent thrombosis: definitions, mechanisms and prevention," Eur. Soc. Cardiol., 5(32) (2007).
Grundy et al., "Diabetes and Cardiovascular Disease : A Statement for Healthcare Professionals From the American Heart Association," Circulation, 100:1134-1146 (1999).
Hayry et al., "Towards understanding the pathophysiology of chronic rejection," Clin. Investigator, 70:780-90 (1992).
Hill et al., "Circulating endothelial progenitor cells as novel biological determinants of vascular function and risk," Can. J. Cardiol., 20 (Suppl B):44B-48B (2004).
Iakovou et al., "Incidence, predictors, and outcome of thrombosis after successful implantation of drug-eluting stents," JAMA, 293(17):2126-2130 (2005).
Idris et al., "Therapeutic angiogenesis for treatment of peripheral vascular disease," Growth Factors, 22(4):269-79 (2004).
International Preliminary Report on Patentability issued in PCT/US2012/028434 issued on Sep. 19, 2013 (5 pages).
Kawamoto et al., "Endothelial Progenitor Cells for Cardiovascular Regeneration," Trends in Cardiovascular Medicine, 18:33-37 (2008).
Kommineni et al., "IFN-gamma acts as anti-angiogenic cytokine in the human cornea by regulating the expression of VEGF-A and sVEGF-R1," Biochemical & Biophysical Research Communications, 374:479-484 (2008).
Liao et al., "Kruppel-like factor 4 regulates macrophage polarization," J. Clin. Invest., (2011).
Luscher et al., "Drug-eluting stent and coronary thrombosis: biological mechanisms and clinical implications," Circulation, 115(8):1051-1058 (2007).
Paul, "Chronic rejection of organ allografts: magnitude of the problem," Transplant. Proc., 25:2024-25 (1993).
Rafii et al., "Therapeutic stem and progenitor cell transplantation for organ vascularization and regeneration," Nature Medicine, 9:702-712 (2003).
Sato et al., "TGF-beta 1 reciprocally controls chemotaxis of human peripheral blood monocyte-derived dendritic cells via chemokine receptors," J. Immunol.,164:2285-2295 (2000).
Schalkwijk and Stehouwer, "Vascular complications in diabetes mellitus: the role of endothelial dysfunction," Clinical Science, 109:143-159 (2005).
Sharples et al., "Risk factor analysis for the major hazards following heart transplantation—rejection, infection, and coronary occlusive disease," Transplantation, 52:244-52 (1991).
Subramaniam et al., "Role of TIEG1 in biological processes and disease states," J. Cell Biochem., 102:539-548 (2007).
Subramaniam et al., "TIEG1 null mouse-derived osteoblasts are defective in mineralization and in support of osteoclast differentiation in vitro," Molecular & Cellular Biology, 25:1191-1199 (2005).
Tateishi-Yuyama et al., "Therapeutic angiogenesis for patients with limb ischaemia by autologous transplantation of bone-marrow cells: a pilot study and a randomised controlled trial," Lancet, 360:427-435 (2002).
Tongers et al., "Therapeutic angiogenesis for critical limb ischemia: microvascular therapies coming of age," Circulation, 118:9-16 (2008).
Ulloa et al., "Inhibition of transforming growth factor-beta/SMAD signalling by the interferongamma/STAT pathway," Nature, 397:710-713 (1999).
Vasa et al., "Number and migratory activity of circulating endothelial progenitor cells inversely correlate with risk factors for coronary artery disease," Circ. Res., 89:E1-7 (2001).
Wara et al., "Bone marrow-derived CMPs and GMPs represent highly functional proangiogenic cells: implications for ischemic cardiovascular disease," Blood, 118(24):6461-4. (2011).
Wara et al., "TGF-β1 signaling and Krüppel-like factor 10 regulate bone marrow-derived proangiogenic cell differentiation, function, and neovascularization," Blood, 118:6450-6460 (2011).
Mark W. Feinberg, M. D., Pilot grants, Awardees 2009, abstract. Retrieved from the Internet: <URL:http://www.baderc.org/feasibility/2009grants.html>, p. 1-2.
Scott T. Robinson. Determining the role of endothelial progenitor cells in post-natal neovascularization. Georgia Institute of Technology, Dec. 2010, p. 8-9.
International Search Report and Written Opinion mailed Jul. 12, 2012 in international application No. PCT/US2012/028434, 6 pgs.

* cited by examiner

US 9,500,658 B2

KRUPPEL-LIKE FACTOR 10 (KLF10) AS A BIOMARKER OF ENDOTHELIAL PROGENITOR CELL DYSFUNCTION

This application is a U.S. National Phase Application under 35 U.S.C. §371 of International Patent Application No. PCT/US2012/028434, filed on Mar. 9, 2012, which claims the benefit of U.S. Provisional Patent Application Ser. No. 61/450,944, filed on Mar. 9, 2011. The entire contents of the foregoing are hereby incorporated by reference.

FEDERALLY SPONSORED RESEARCH OR DEVELOPMENT

This invention was made with Government support under Grant Nos. HL080174, HL091076, HL088819, DE014036, and HL075771 awarded by the National Institutes of Health. The Government has certain rights in the invention.

TECHNICAL FIELD

This invention relates to the use of Krüppel-like Factor (KLF10) as a diagnostic and prognostic tool for peripheral artery disease and other disease conditions associated with reduced angiogenesis or endothelial progenitor cell dysfunction such as such as ischemic coronary artery disease, ischemic cardiomyopathy, diabetic vasculopathy, transplantation arteriosclerosis, and stent thrombosis.

BACKGROUND

Accumulating evidence suggests that in healthy individuals, circulating endothelial progenitor cells, broadly defined as pro-angiogenic cells (PACs), represent a population of bone marrow (BM)-derived stem and progenitor cells responsible for repairing injured tissue and initiating neovasculogenesis (Kawamoto et al., Trends in Cardiovascular Medicine. 2008, 18:33-37; Burt et al., JAMA. 2008, 299: 925-936). Potentiation of PAC mobilization, homing, or adhesion, has been shown to ameliorate the development of ischemic injury in animal models (Kawamoto et al., Trends in Cardiovascular Medicine. 2008, 18:33-37; Burt et al., JAMA. 2008, 299:925-936). In addition, blockade of pro-angiogenic cytokines or their signaling pathways is believed to alter PAC function and lead to impaired angiogenesis in response to vascular injury and in end-organ ischemia (Kawamoto et al., Trends in Cardiovascular Medicine. 2008, 18:33-37; Burt et al., JAMA. 2008, 299:925-936). Indeed, reduced levels of circulating PACs and diminished PAC function have been reported and found to correlate with a wide-spectrum of atherosclerotic vascular diseases, including peripheral artery disease (PAD) (Fadini et al., Arterioscler Thromb Vasc Biol. 2006, 26:2140-2146; Vasa et al., Circ Res. 2001, 89:E1-7; Hill et al., [see comment] [reprint in Can J. Cardiol. 2004 August; 20 Suppl B:44B-48B; PMID: 15309205]. New England Journal of Medicine. 2003, 348:593-600).

Several early phase I/II trials have been conducted to assess the efficacy of cell-based therapies to treat patients with PAD, but have yielded mixed results (Kawamoto et al., Trends in Cardiovascular Medicine. 2008, 18:33-37; Burt et al., JAMA. 2008, 299:925-936; Tongers et al., Circulation. 2008, 118:9-16; Tateishi-Yuyama et al., Lancet. 2002, 360: 427-435; Rafii et al., Nature Medicine. 2003, 9:702-712; Devanesan et al., Eur J Vasc Endovasc Surg. 2009, 38:475-481). Identification of specific PAC subtypes that are endowed with superior capacity to promote neovascularization may represent a particularly efficacious therapeutic strategy. Among hematopoietic progenitor stem cells, the common myeloid progenitors (CMPs) and granulocyte-macrophage progenitors (GMPs) constitute a population of bone marrow-derived cells that preferentially differentiate into PACs and possess robust angiogenic activity under ischemic conditions in vivo (Wara et al., Blood 2011 Dec. 8; 118(24): 6461-4. Epub 2011 Aug. 9). However, the signaling pathways and downstream factors that mediate these pro-angiogenic functions remain poorly understood.

SUMMARY

The present invention is based, at least in part, on the discovery that a TGF-beta 1-responsive Krüppel-like Factor, KLF10, is strongly expressed in PACs derived from CMPs and GMPs, ~60-fold higher than in progenitors lacking PAC markers. In addition, KLF10 expression was found to be significantly reduced in PACs from patients with peripheral artery disease, diabetes, and stent thrombosis. Collectively, these observations identify KLF10 as a diagnostic marker of peripheral artery disease and other disease conditions associated with reduced angiogenesis or endothelial progenitor cell dysfunction such as ischemic coronary artery disease, ischemic cardiomyopathy, diabetic vasculopathy, transplantation arteriosclerosis, and stent thrombosis.

Thus, in a first aspect, the invention provides methods for predicting risk of developing or diagnosing the presence of peripheral artery disease (PAD) in a subject. The methods include determining a level of Krüppel-like Factor (KLF10) expression in a sample comprising peripheral blood cells from the subject; and comparing the level of KLF10 in the sample to a reference level of KLF10. The presence of a level of KLF10 in the sample below the reference level indicates that the subject has or is at risk of developing PAD.

In another aspect, the invention provides methods for predicting risk of developing or diagnosing the presence of stent thrombosis in a subject. The methods include determining a level of Krüppel-like Factor (KLF10) expression in a sample comprising peripheral blood cells from the subject; and comparing the level of KLF10 in the sample to a reference level of KLF10. The presence of a level of KLF10 in the sample below the reference level indicates that the subject has or is at risk of developing stent thrombosis.

In another aspect, the invention provides methods for predicting risk of developing or diagnosing the presence of diabetic vasculopathy in a subject, e.g., a subject who has or is at risk of developing diabetes, e.g., type 2 diabetes. The methods include determining a level of Krüppel-like Factor (KLF10) expression in a sample comprising peripheral blood cells from the subject; and comparing the level of KLF10 in the sample to a reference level of KLF10. The presence of a level of KLF10 in the sample below the reference level indicates that the subject has or is at risk of developing diabetic vasculopathy.

In another aspect, the invention provides methods for predicting risk of developing or diagnosing the presence of ischemic coronary artery disease, ischemic cardiomyopathy, or transplantation arteriosclerosis in a subject. The methods include determining a level of Krüppel-like Factor (KLF10) expression in a sample comprising peripheral blood cells from the subject; and comparing the level of KLF10 in the sample to a reference level of KLF10. The presence of a level of KLF10 in the sample below the reference level indicates that the subject has or is at risk of developing ischemic coronary artery disease, ischemic cardiomyopathy, or transplantation arteriosclerosis.

In the methods described herein, a diagnosis or an increased risk of a particular condition can be determined by the presence of symptoms or risk factors consistent with that condition, plus an elevated level of KLF10. Symptoms and risk factors of each of these conditions are known in the art and/or described herein.

In some embodiments, the peripheral blood cells are pro-angiogenic cells (PACs), e.g., CD34+/VEGFR2+. In some embodiments, determining a level of KLF10 expression comprises detecting a level of KLF10 protein in the sample.

In some embodiments, the reference level represents a threshold, wherein levels below the threshold are associated with the presence of, or increased risk of developing, PAD, stent thrombosis, diabetic vasculopathy, ischemic coronary artery disease, ischemic cardiomyopathy, or transplantation arteriosclerosis.

In some embodiments, the subject has or is at risk of developing diabetes, and the presence of a level of KLF10 below the threshold indicates that the subject has or is at increased risk of developing diabetic vasculopathy.

In some embodiments, the subject has, or has an increased risk of developing, PAD, stent thrombosis, diabetic vasculopathy, ischemic coronary artery disease, ischemic cardiomyopathy, or transplantation arteriosclerosis, and the method further comprises administering a treatment for PAD, stent thrombosis, diabetic vasculopathy, ischemic coronary artery disease, ischemic cardiomyopathy, or transplantation arteriosclerosis to the subject.

In some embodiments, the methods include determining a level of Krüppel-like Factor (KLF10) expression in a subsequent sample comprising peripheral blood cells from the subject; and comparing the level of KLF10 in the subsequent sample to the level of KLF10 in the earlier sample. An increase in a level of KLF10 in the subsequent sample as compared to the earlier sample indicates that the treatment is effective.

In some embodiments, the level of KLF10 is correlated with severity of the condition, and thus the methods can include determining the severity of a disease condition associated with reduced angiogenesis or endothelial progenitor cell dysfunction, e.g., peripheral artery disease, ischemic coronary artery disease, ischemic cardiomyopathy, diabetic vasculopathy, transplantation arteriosclerosis, or stent thrombosis, based on the level of KLF10 in the sample; the level can be compared to reference levels, e.g., reference ranges, that represent differing levels of severity. For example, in some embodiments, the lower the level of KLF10 in the sample, the more severe the condition is.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
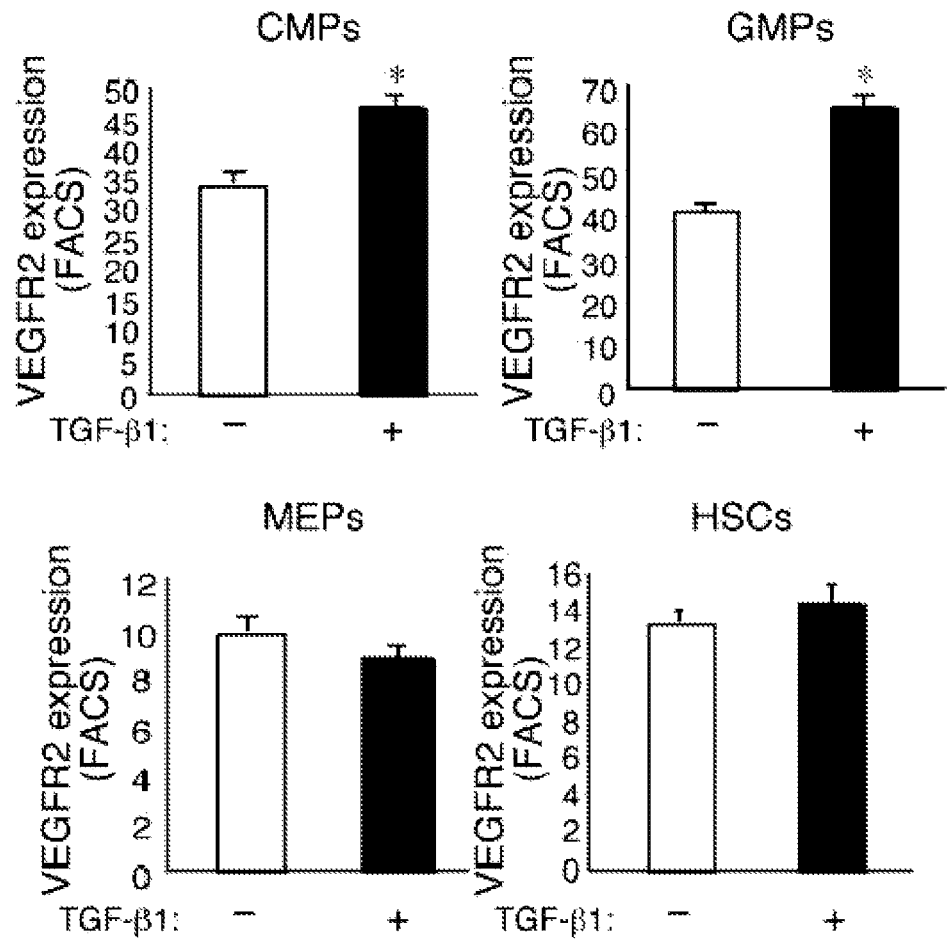
FIGS. 1A-F. TGF-β1 regulates PAC differentiation and function. (A) VEGFR2 expression in bone marrow-derived progenitors isolated from WT mice (A) or TGF-b1$^{+/+}$ or TGF-b1$^{+/-}$ (B) and grown in the presence or absence of TGF-b1 (A) for 7 days (n=3 per group). Percent VEGFR2 expression was analyzed by flow cytometry. *P<0.01 vs. no TGF-b1; **P<0.01 vs. vs. TGF-b1$^{+/-}$. (C) Bone marrow-derived progenitors grown in the presence of Ctrl (vehicle) or TGF-b1 and plated in fibronectin-coated wells were assessed for adhesion (n=6 per group). HPF, high power field; *P<0.05 vs. Ctrl. (D) Bone marrow-derived GMPs and MEPs were grown in the presence or absence of TGF-b1 treatment were assessed for VEGFR2 mRNA expression by qPCR (n=3 per group). *P<0.01 vs. Ctrl; **P<0.05 vs. Ctrl. (E) TGF-b1 stimulated expression of the VEGFR2 promoter-luciferase reporter transfected in bone marrow-derived GMPs and MEPs (n=3 per group). *P<0.01 vs. Ctrl; **P<0.05 vs. Ctrl. (F) Effect of IFN-γ on CMP- and GMP-derived PAC differentiation. Bone marrow-derived progenitors were isolated and grown in endothelial growth medium-2 (EGM-2) medium in the presence or absence of IFN-γ for 7 days (n=3 per group). Percent VEGFR2 expression was analyzed by flow cytometry. IFN-γ reduced VEGFR2 expression by 29% and 73% in CMP- and GMP-derived PACs, respectively. *P<0.01 vs. no IFN-γ.

The pleiotropic transforming growth factor (TGF)-b1 plays an important role in cell growth, differentiation, and activation in a number cell types (Feinberg et al., Panminerva Medica. 2005, 47:169-186). TGF-b1 has been shown to contribute to various aspects of neovascularization including cell adhesion, migration, and homing. These effects may be mediated in part by induction of integrins, chemokine receptors, or responsiveness to important growth factors for cell homing such as stromal cell-derived factor-1 (SDF-1) (Capron et al., Blood. 2010, 116:1244-1253; Franitza et al., Eur J Immunol. 2002, 32:193-202; Sato et al., J. Immunol. 2000, 164:2285-2295; Basu et al., Blood. 2005, 106:485-493). Thus, controlled modulation of TGF-b1 and its downstream signaling pathways may allow for fine-tuning of the angiogenic response, perhaps through mechanisms related to PAC differentiation or function.

Krüppel-like factors (KLFs), a subclass of the zinc-finger family of transcription factors, participate in various aspects of cellular growth, development, and differentiation (Cao et al., Blood. 2010; Feinberg et al., Trends Cardiovasc Med. 2004, 14:241-246). KLFs are characterized by a DNA-binding domain that contains three C2H2-type zinc fingers capable of binding to either a CACCC-element or GC-box in the promoter region of target genes thereby regulating transcriptional activity and gene expression. Gene-targeting studies have implicated KLFs as important in immune and hematopoietic cell biology (Cao et al., Blood. 2010; Feinberg et al., Trends Cardiovasc Med. 2004, 14:241-246). Because of the critical role played by KLFs in the development of different hematopoietic lineages, it was hypothesized that a related Krüppel-like zinc-finger protein may regulate the differentiation and/or function of CMP- or GMP-derived PACs and thus regulate angiogenesis.

Krüppel-like Factor (KLF10) Regulates Transforming Growth Factor Beta 1 (TGF-b1)

The studies described herein provide evidence that in response to TGF-b1, KLF10 plays an important role in controlling CMP- and GMP-derived PAC differentiation and function in vitro and in vivo. Notably, KLF10−/− CMP- and GMP-derived PACs possess multiple defects in effector functions including adhesion, migration, and elaboration and/or expression of chemokines, chemokine receptors, and integrins critical to neovascularization. In addition, KLF10−/− mice display reduced levels of circulating PACs and impaired blood flow recovery after hindlimb ischemia, an effect rescued by wild-type (WT) PACs but not by KLF10−/− PACs. Mechanistically, KLF10 targets VEGFR2 which may explain, in part, these effects. Importantly, KLF10 expression was found to be reduced in PACs from patients with peripheral artery disease. Taken together, these observations indicate that KLF10 acts as a key transcriptional regulator of TGF-b1 in PAC differentiation and function and represents a diagnostic marker for angiogenesis.

Methods of Diagnosing or Predicting Risk Based on KLF10 Expression

Included herein are methods for diagnosing and predicting risk of developing conditions associated with reduced angiogenesis or endothelial progenitor cell dysfunction such as PAD, ischemic coronary artery disease, ischemic cardiomyopathy, diabetic vasculopathy, transplantation arteriosclerosis, and stent thrombosis. The methods include obtaining a sample comprising (e.g., enriched in) peripheral blood cells, e.g., enriched in pro-angiogenic cells (PACs), e.g., enriched in CD34$^+$/VEGFR2$^+$ PACs, (e.g., PACS isolated by FACS or magnetic bead separation specific for the cell surface markers, e.g., using antibodies directed toward CD34 and/or VEGFR2) from a subject, and evaluating the presence and/or level of KLF10 in the sample, and comparing the presence and/or level with one or more references levels. In some embodiments, the sample includes a biological fluid, e.g. blood, serum, plasma, saliva, and/or urine.

The presence and/or level of a protein can be evaluated using methods known in the art, e.g., using quantitative immunoassay methods, ELISA, enzymatic assays, flow cytometry with or without cell permeabilization, spectrophotometry, colorimetry, fluorometry, bacterial assays, liquid chromatography, gas chromatography, mass spectrometry, gas chromatography-mass spectrometry (GC-MS), liquid chromatography-mass spectrometry (LC-MS), LC-MS/MS, tandem MS, high pressure liquid chromatography (HPLC), HPLC-MS, and nuclear magnetic resonance spectroscopy, or other known techniques for determining the presence and/or quantity of a protein. The presence and/or level of a nucleic can be evaluated using methods known in the art, e.g., using quantitative PCR methods. In some embodiments, high throughput methods, e.g., protein or gene chips as are known in the art (see, e.g., Ch. 12, Genomics, in Griffiths et al., Eds. *Modern genetic Analysis,* 1999, W.H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual,* Cold Spring Harbor Laboratory Press; 2002; Hardiman, *Microarrays Methods and Applications: Nuts & Bolts,* DNA Press, 2003), can be used to detect the presence and/or level of KLF10 in a sample.

In some embodiments, the presence and/or level of KLF10 is comparable to the presence and/or level of the protein(s) in the disease reference, and the subject has one or more symptoms associated with PAD, ischemic coronary artery disease, ischemic cardiomyopathy, diabetic vasculopathy, transplantation arteriosclerosis, and stent thrombosis, then the subject is diagnosed with PAD, ischemic coronary artery disease, ischemic cardiomyopathy, diabetic vasculopathy, transplantation arteriosclerosis, or stent thrombosis. In some embodiments, the subject has no overt signs or symptoms of PAD, diabetes (e.g., of vascular complications of diabetes), ischemic coronary artery disease, ischemic cardiomyopathy, diabetic vasculopathy, transplantation arteriosclerosis, or stent thrombosis, but the presence and/or level of one or more of the proteins evaluated is comparable to the presence and/or level of the protein(s) in the disease reference, then the subject has an increased risk of developing PAD, ischemic coronary artery disease, ischemic cardiomyopathy, diabetic vasculopathy, transplantation arteriosclerosis, and stent thrombosis.

Suitable reference values can be determined using methods known in the art, e.g., using standard clinical trial methodology and statistical analysis. The reference values can have any relevant form. In some cases, the reference comprises a predetermined value for a meaningful level of KLF10, e.g., a control reference level that represents a normal level of KLF10, e.g., a level in an unaffected subject or a subject who is not at risk of developing a disease described herein, and/or a disease reference that represents a level of the proteins associated with conditions associated with reduced angiogenesis or endothelial progenitor cell dysfunction, e.g., a level in a subject having PAD, ischemic coronary artery disease, ischemic cardiomyopathy, diabetic vasculopathy, transplantation arteriosclerosis, and stent thrombosis.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein (e.g., PAD, ischemic coronary artery disease, ischemic cardiomyopathy, diabetic vasculopathy, transplantation arteriosclerosis, or stent thrombosis). In some cases it may be desirable that the control subject is a diabetic (e.g., a diabetic who does not have vascular complications), and in other cases it may be desirable that a control subject is a non-diabetic. In some cases it may be desirable that the control subject has a stent, and in other cases it may be desirable that a control subject does not have a stent.

A disease reference subject is one who has (or has an increased risk of developing) one or more of PAD, ischemic cardiomyopathy, diabetic vasculopathy, transplantation arteriosclerosis, or stent thrombosis). An increased risk is defined as a risk above the risk of subjects in the general population.

Thus, in some cases the level of KLF10 in a subject being less than or equal to a reference level of KLF10 is indicative of a clinical status (e.g., indicative of a disorder as described herein, e.g., PAD, ischemic coronary artery disease, ischemic cardiomyopathy, diabetic vasculopathy, transplantation arteriosclerosis, or stent thrombosis). In other cases the level of KLF10 in a subject being greater than or equal to the reference level of KLF10 is indicative of the absence of disease or normal risk of the disease. In some embodiments, the amount by which the level in the subject is the less than the reference level is sufficient to distinguish a subject from a control subject, and optionally is a statistically significantly less than the level in a control subject. In cases where the level of KLF10 in a subject being equal to the reference level of KLF10, the "being equal" refers to being approximately equal (e.g., not statistically different).

The predetermined value can depend upon the particular population of subjects (e.g., human subjects) selected. For example, an apparently healthy population will have a different 'normal' range of levels of KLF10 than will a population of subjects which have, or are likely to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

Subjects, as used herein, includes mammals, e.g., human and non-human primates, as well as veterinary subjects and experimental animals.

The methods described herein are useful for diagnosing and predicting risk of developing conditions associated with reduced angiogenesis or endothelial progenitor cell dysfunction such as PAD, ischemic coronary artery disease, ischemic cardiomyopathy, diabetic vasculopathy, transplantation arteriosclerosis, and stent thrombosis. In some embodiments, once it has been determined that a person has PAD, ischemic coronary artery disease, ischemic cardiomyopathy, diabetic vasculopathy, transplantation arteriosclerosis, or stent thrombosis, or has an increased risk of developing PAD, ischemic coronary artery disease, ischemic cardiomyopathy, diabetic vasculopathy, transplantation arteriosclerosis, or stent thrombosis, then a treatment, e.g., as known in the art or as described herein, can be administered.

PAD

The invention, in some aspects, relates to methods, compositions and kits useful for diagnosing and determining risk of developing peripheral Artery Disease (which as used herein include peripheral vascular disease or PVD), which is characterized by the presence of impaired circulation to the limbs, typically as a result of the presence of atherosclerotic plaques. Subjects with PAD have a very high risk of fatal and non-fatal cerebrovascular and cardiovascular events.

Once a subject has been identified as having or at an increased risk of developing PAD by a method described herein, treatment, e.g., anti-coagulation therapy (e.g., antiplatelet therapy), angiotensin-converting enzyme (ACE) inhibitors and antiotensin receptor blockers (ARBs), or lipid-lowering agents, e.g., statins and/or fibrates or niacin, angioplasty, thrombolytic therapy, or surgical interventions such as bypass surgery, atherectomy, or amputation of the affected limb, can be administered. The methods can be performed multiple times as well to detect whether an increase in risk of PAD, is increasing over time, or whether any therapy is effective in treating the condition or decreasing risk. See, e.g., Idris et al., Growth Factors. 2004 December; 22(4):269-79; Coppola et al., Vasc Health Risk Manag. 2008 December; 4(6): 1179-1187.

Diabetic Vasculopathy

The invention, in some aspects, relates to methods, compositions and kits useful for diagnosing and determining risk of developing vascular complications of diabetes, i.e., diabetic vasculopathy. Diabetes is often associated with endothelial dysfunction which lead to vascular complications, thus in some embodiments, the methods can be used to predict a subject's risk of developing vascular complications of diabetes, e.g., macrovascular complications (coronary artery disease, peripheral arterial disease, and stroke) and/or microvascular complications (diabetic nephropathy, neuropathy, and retinopathy). See, e.g., Fowler et al., Clinical Diabetes April 2008 vol. 26 no. 2 77-82; Schalkwijk and Stehouwer, Clinical Science (2005) 109, 143-159.

In some embodiments, the subject has been diagnosed with diabetes or another disorder of glucose regulation, e.g., insulin resistance, metabolic syndrome or hyperglycemia.

As used herein diabetes (also referred to as diabetes mellitus), refers to any one of a number of exemplary classes (or types) of glucose-related metabolic disorders. Diabetes includes, but is not limited to the following classes (or types): type I diabetes mellitus, type II diabetes mellitus, gestational diabetes, and other specific types of diabetes. Glucose-related metabolic disorders also include prediabetic conditions, such as those associated with impaired fasting glycemia and impaired glucose tolerance. Glucose-related metabolic disorders are often associated with symptoms in a subject such as increased thirst and urine volume, recurrent infections, unexplained weight loss and, in severe cases, drowsiness and coma; high levels of glycosuria are often present. Children suspected of having a glucose-related metabolic disorder may, in some cases, present with severe symptoms, such as high blood glucose levels, glycosuria, and/or ketonuria.

Type 1 diabetes is usually due to autoimmune destruction of the pancreatic beta cells. Type 2 diabetes is characterized by insulin resistance in target tissues, which may result in a need for abnormally high amounts of insulin and diabetes develops when the beta cells cannot meet this demand. Gestational diabetes is similar to type 2 diabetes in that it involves insulin resistance; the hormones of pregnancy can cause insulin resistance in women genetically predisposed to developing this condition. Other specific types of diabetes are known in the art and disclosed in Definition, Diagnosis and Classification of Diabetes Mellitus and its Complications, Report: WHO/NCD/NCS/99.2 by the World Health Organisation, Department of Noncommunicable Disease Surveillance (1999), the contents of which are incorporated herein in their entirety by reference.

In some embodiments, subject has Type 2 diabetes. Type 2 is also referred to as non-insulin-dependent diabetes or adult-onset diabetes, and is characterized by disorders of insulin action and insulin secretion, either of which may be the predominant feature. Both are usually present at the time that this form of diabetes is clinically manifest.

In some embodiments, the subject has gestational hyperglycemia or gestational diabetes. These are forms of diabetes associated with pregnancy. Gestational diabetes is associated with carbohydrate intolerance resulting in hyperglycemia of variable severity with onset or first recognition during pregnancy. Thus, it does not exclude the possibility that the glucose intolerance may antedate the pregnancy but was previously unrecognized. The classification typically applies irrespective of whether or not insulin is used for treatment or the condition persists after pregnancy.

In some embodiments, the subject has "metabolic Syndrome" which is often characterized by hypertension, central (upper body) obesity, and dyslipidaemia, with or without hyperglycaemia. Subjects with the Metabolic Syndrome are at high risk of macrovascular disease. Often a person with abnormal glucose tolerance will be found to have at least one or more of the other cardiovascular disease (CVD) risk components. The Metabolic Syndrome is also referred to as Syndrome X and the Insulin Resistance Syndrome. Epidemiological studies confirm that this syndrome occurs commonly in a wide variety of ethnic groups including Caucasians, African-Americans, Mexican-Americans, Asian Indians, Chinese, Australian Aborigines, Polynesians and Micronesians. The Metabolic Syndrome with normal glucose tolerance identifies a subject as a member of a group at very high risk of diabetes. Thus, vigorous early management of the syndrome may have a significant impact on the prevention of both diabetes- and cardiovascular disease.

Once a subject has been identified as at an increased risk of developing diabetes, e.g., vascular complications of diabetes, by a method described herein, treatment can be administered.

In some embodiments, a treatment is administered to the subject comprising an effective amount of at least one anti-diabetes compound and/or instructing the subject to adopt at least one anti-diabetic lifestyle change. Anti-diabetes compound are well known in the art and some are disclosed herein. Non-limiting examples include alpha-glucosidase inhibitors for example acarbose and miglitol; biguanides for example metformin, phenformin, and buformin; meglitinides for example, repaglinide and nateglinide; sulfonylureas, for example tolbutamide, chlorpropamide, tolazamide, acetohexamide, glyburide, glipizide, glimepiride, and gliclazide; thiazolidinediones, for example troglitazone, rosiglitazone, and pioglitazone; peptide analogs, for example glucagon-like peptide I (GLP1) and analogs thereof (e.g., Exentide, Extendin-4, Liraglutide, gastric inhibitory peptide (GIP) and analogs thereof; vanadates (e.g., vanadyl sulfate); GLP agonists; DPP-4 inhibitors, for example vildagliptin and sitagliptin; dichloroacetic acid; amylin; carnitine palmitoyltransferase inhibitors; B3 adrenoceptor agonists; and insulin. Appropriate anti-diabetic lifestyle changes are also well known in the art. Non-limiting examples include increased physical activity, caloric and/or carbohydrate intake restriction, nutritional meal planning, and weight reduction.

In some embodiments, the methods also include the administration of anti-hypertensives, e.g., angiotensin-converting enzyme (ACE) inhibitors and antiotensin receptor blockers (ARBs), or lipid-lowering agents, especially statins and/or fibrates or niacin. See, e.g., Fowler et al., Clinical Diabetes April 2008 vol. 26 no. 2 77-82; Grundy et al., Circulation 1999, 100:1134-1146 (especially Table 5 therein).

Stent Thrombosis

The invention, in some aspects, relates to methods, compositions and kits useful for diagnosing and determining risk of developing stent thrombosis. Stent thrombosis occurs when platelet adhesion and activation inside a stent lead to thrombus formation. Stent thrombosis can occur early (0-30 days), late (more than 30 days), or very late (more than 12 months) after stent implantation. Stent thrombosis can also be characterized as acute (less than 24 hours after stent implantation) or subacute (1-30 days after stent implantation). The presence of stent thrombosis can sometimes be confirmed by symptoms suggestive of an acute coronary syndrome and angiographic or pathologic confirmation of stent thrombosis, but in some cases angiographic confirmation is not possible. The present methods are useful in predicting whether a subject who has had one or more stents implanted has an increased risk of developing stent thrombosis. Other risk factors can also be considered, e.g., procedure- and lesion-related factors, including: use of multiple stents; small vessel diameter; coronary dissection; geographic miss; slow flow; long lesions; stent malapposition; underexpansion of the stent; stent design (strut thickness and polymer type); and/or bifurcation of lesions; patient factors, including diabetes; Acute Coronary Syndromes (e.g., STEMI); left ventricular dysfunction; renal failure; advanced age; and/or high platelet reactivity; or factors relating to the anti-platelet therapy, such as inadequate intensity of therapy (e.g., absence of dual platelet inhibition or insufficient dosage); patient non-compliance with therapy; and/or premature cessation of anti-platelet therapy; see Grove and Kristensen, "Stent thrombosis: definitions, mechanisms and prevention," Eur. Soc. Cardiol. 5(32) May 2007; Iakovou et al., JAMA 2005; 293(17):2126-2130; Luscher et al., Circulation 2007; 115(8):1051-1058.

Once a subject has been identified as at an increased risk of developing stent thrombosis by a method described herein, treatment, e.g., intensified anti-coagulation therapy (e.g., dual anti-platelet therapy), can be administered. The methods described herein can be performed, e.g., 12, 24, or 48 hours after stent implant, or 1, 2, 3, 4, or more weeks after stent implant. The methods can be performed multiple times as well to detect whether an increase in risk of stent thrombus, or stent thrombus formation, is increasing over time, or whether any therapy, e.g., anti-coagulation therapy, is effective in decreasing risk.

Ischemic Coronary Artery Disease

Coronary artery disease (CAD) is the result of accumulation of atheromatous plaques within the coronary arteries that supply the myocardium, leading to ischemia of the myocardial tissues. Subjects with CAD have a very high risk of fatal and non-fatal cerebrovascular and cardiovascular events.

Ischemic Cardiomyopathy

Ischemic cardiomyopathy is characterised by the presence of significantly impaired left ventricular function (i.e., a left ventricular ejection fraction of ≤35 to 40 percent) resulting from coronary artery disease, and can be diagnosed in patients with heart failure (HF) who have had a myocardial infarction (MI) or have evidence of hibernating myocardium or severe coronary disease (e.g., identified by angiography). See, e.g., Felker et al, J Am Coll Cardiol. 2002; 39(2):210.

Transplant Arteriosclerosis

Transplant arteriosclerosis, or transplantation arteriosclerosis, is an alloimmune-initiated vascular stenosis that is a significant cause of allograft failure in cardiac and other solid organ transplants (Billingham, Transplant Proc., 1989, 21:3665-66, and Sharples et al., Transplantation, 1991, 52:244-52; Paul, Transplant. Proc., 1993, 25:2024-25, and Hayry et al., Clin. Investigator, 1992, 70:780-90). See, e.g., U.S. Pat. No. 5,675,062 and references cited therein.

EXAMPLES

The invention is further described in the following examples, which do not limit the scope of the invention described in the claims.

Material and Methods

The following Materials and Methods were used in the Examples set forth below.

Mice

KLF10$^{-/-}$ mice, were previously described (Subramaniam et al., Molecular & Cellular Biology. 2005, 25:1191-1199) and TGF-b1$^{+/-}$/Rag2$^{-/-}$ mice were obtained from the National Cancer Institute Mouse Repository (Frederick, Md., USA). Mouse genotypes were verified by PCR. Mice aged 8-12 weeks were used for most experiments.

Isolation and in vitro Differentiation of PACs CMPs, GMPs, megakaryocyte-erythrocyte progenitors (MEPs), and hematopoietic stem cells (HSCs) were isolated from C57BL/6 mice and KLF10$^{-/-}$ mice bone marrow by using multicolor FACS (BD ARIAFACS; Beckton-Deckinson, Biosciences, San Diego, Calif., USA) as previously described (Feinberg et al., EMBO Journal. 2007, 26:4138-4148). Single-cell suspensions were prepared from BM and red cells were lysed with red cell lysis solution (Qiagen, Valencia, Calif., USA). Briefly, ~2-5×10$^5$ bone marrow-derived cells were prospectively isolated and purified as follows: HSCs (Lin$^-$Sca1$^+$c-kit$^+$), CMPs (Lin$^-$Sca1$^-$c-kit$^+$CD34$^+$FcγRII/II$^{lo}$), GMPs (Lin$^-$Sca1$^-$c-kit$^+$CD34$^+$FcγRII/III$^{hi}$), and MEPs (Lin$^-$Sca1$^-$c-kit$^+$CD34$^-$FcγRII/III$^{lo}$) (CellQuest). HSCs, CMPs, GMPs, and MEPs were incubated in endothelial growth media (EGM-2) or Iscove's Modified Dulbecco's Media (IMDM) for 8-10 days where indicated, and subjected to FACS to determine expression for VEGFR2, CXCR4, CXCR3, or CCR7 (eBioscience). All flow cytometry analyses were performed using 10,000 cell events.

In vivo Subcutaneous Matrigel Plug

The subcutaneous Matrigel plug mouse model was generated from 8- to 10-week old male WT or KLF10$^{-/-}$ mice. Matrigel plugs that had been admixed with 0.8 mL of Matrigel (BD Biosciences, Rockville, Md., USA), bFGF (250 ng per mL; R&D Systems, Minneapolis, Minn., USA), and heparin (60 units per mL; Hospira, Inc., Lake Forrest, Ill., USA), were implanted subcutaneously. Mice were euthanized 8 days after Matrigel implantation at which time the intact Matrigel plugs were removed, embedded in paraffin, and sectioned for detection of angiogenesis using an anti-mouse CD31 antibody (eBioscience, San Diego, Calif., USA).

Hindlimb Ischemia

Ischemic injury was produced by unilateral femoral artery ligation in C57BL/6 mice. The right femoral artery was isolated under direct visualization. Proximal and distal sutures were tied around the femoral artery relative to the origin of the deep femoral artery. The deep femoral artery was cauterized and the complete severance of the main femoral artery was performed between the two ligatures. Immediately after surgery, mice were imaged on a 785 nm near-infrared Laser Doppler Imager-2 (Moor Instruments, Inc., Devon, UK). In some studies, the relevant bone marrow-derived PACs from WT or KLF10$^{-/-}$ mice were injected intramuscularly (i.m.) into KLF10$^{-/-}$ or WT mice into the right quadriceps immediately after surgery. Images of paraffin sections (5 μm) of quadriceps muscles were scanned using an AQUA/PM2000 Imaging Platform and Spotgrabber software suite version 2.2 (HistoRx, New Haven, Conn., USA) and exported through AQUA automated analysis software (HistoRX). For confocal microscopy, images were acquired using an Olympus Fluoview (Model FV1000; Essex, UK) camera and accompanying FV10-ASW software version 02.01.

Antibodies and Recombinant Proteins

Polyclonal KLF10 antibody was used as described (Subramaniam et al., Molecular & Cellular Biology. 2005; 25:1191-1199). Recombinant TGF-b1 (Peprotech, Rocky Hill, N.J., USA) and IFN-γ (R&D Systems, Minneapolis, Minn., USA) were used for some PAC differentiation assays. Cellular protein extraction and Western blot analyses were performed as described (Cao et al., J Biol Chem. 2009; 284:24914-24924).

Flow Cytometry

PACs were washed, resuspended in PBS plus 2% FBS, and stained for 20 min on ice with directly conjugated (either PE or FITC) monoclonal antibodies specific for VEGFR2, Sca-1 (clone D7), CD31, AC133, Tie-2, Integrin α4, Integrin α5, Integrin α6, Integrin α1, chemokine receptors CXCR4, CXCR3, or CCR7 as described by the manufacturer's protocol (eBioscience, San Diego, Calif., USA). FACS analysis was performed on an LSR-II (Beckton-Deckinson, San Diego, Calif.) and analyzed with BD CellQuest software. For isolation and in vitro differentiation of PACs, ~2-5×10$^5$ bone marrow-derived cells were prospectively isolated and purified as follows: HSCs (Lin$^-$Sca1$^+$c-kit$^+$), CMPs (Lin$^-$Sca1$^-$c-kit$^+$CD34$^+$FcγRII/II$^{lo}$), GMPs (Lin$^-$Sca1$^-$c-kit$^+$CD34$^+$FcγRII/III$^{hi}$), and MEPs (Lin$^-$Sca1$^-$c-kit$^+$CD34$^-$FcγRII/III$^{lo}$) (CellQuest). HSCs, CMPs, GMPs, and MEPs were incubated in endothelial growth media (EGM-2) or Iscove's Modified Dulbecco's Media (IMDM) for 8-10 days where indicated, and subjected to FACS to determine expression for VEGFR2, CXCR4, CXCR3, or CCR7 (eBioscience). All flow cytometry analyses were performed using 10,000 cell events.

Quantitative Real-time PCR.

Total RNA from GMPs$^-$ and MEPs were isolated using Trizol reagent (Invitrogen, Carlsbad, Calif., USA) as previously described (Cao et al., J Biol Chem. 2009; 284:24914-24924). The real-time PCR was performed in triplicate with Brilliant SYBR green mix using Stratagene Mx3000P Real-Time PCR system (Agilent Technologies, Santa Clara, Calif., USA). Beta-actin was used to normalize the samples. Primer sequences were: mouse (m) VEGFR2, 5'-GCAAAACACTCACCATTCCCA-3' (forward; SEQ ID NO:1) and 5'-GAGGTTTGAAATCGACCCTCG-3' (reverse; SEQ ID NO:2); mKLF10, 5'-ATGCTCAACTTCG-GCGCTT-3' (forward; SEQ ID NO:3) and 5'-CGCTTC-CACCGCTTCAAAG-3' (reverse; SEQ ID NO:4) for mKLF10.

PAC Adhesion, Migration, and Wound Closure Assays

Migration assay was performed using the ChemoTx transwell system (Neuro Probe, Inc, Cabin John, Md., USA) according to the manufacturer's protocol. Briefly, 20000 cells suspended in serum-free media were placed in the upper compartment, while the lower compartment was filled with 35 μl of EGM-2 medium containing 2% serum. After 6 hours of incubation at 37° C., cell migration was detected by counting the number of cells in the lower compartment. Each sample was assayed in triplicate. For adhesion assays, the distinct populations of PACs (CMPs, GMPs, MEPs and HSCs grown in EGM-2 for 7 days) were added (20000 cells per well) to fibronectin-coated 24-well plates (Sigma, St. Louis, Mo., USA). After 15 minutes of incubation at 37° C., unattached cells were removed by washing with PBS, and the number of attached cells was quantitated. Conditioned medium from the relevant bone marrow-derived PACs was added to HUVEC confluent monolayers that contained a single would (scratch) induced by a pipette tip. The extent of wound 'closure' after 24 hours was quantitated by Image J software analysis (NIH) and expressed as percent of wound remaining.

Retroviral Transduction and Responsiveness to TGF-b1.

For retroviral studies, mKLF10 cDNA was cloned into the retroviral vector GFP-RV (gift from K Murphy, St. Louis, Mo.) and the retrovirus generated as described before (Cao et al., J Biol Chem. 2009; 284:24914-24924). For retroviral infection, the indicated bone marrow-derived PACs from TGF-b1$^{+/+}$ or TGF-b1$^{+/-}$ mice were transduced as previously described (Cao et al., J Biol Chem. 2009; 284:24914-24924). Flow cytometry was performed 5 days later using PE-conjugated antibodies specific to VEGFR2 (eBioscience).

Transient Transfection Reporter Assays.

GMP- and MEP-derived PACs were cultured in 6-well plates (2×10$^6$ per well) and co-transfected with the VEGFR2 promoter, pcDNA3, or KLF10 in the presence or absence of TGF-b1 by using Amaxa Nucleofector (Program X-001; Lonza, Walkersville, Md., USA) for 24 hours, as described by the manufacturer's protocol. In brief, 4 µg of total plasmid DNA was used in the experiments. Luciferase activity was normalized to beta-galactosidase activity by cotransfecting the pCMV-gal plasmid (0.5 µg) in all experiments. All transfections were performed in triplicate from at least two independent experiments.

Chromatin Immunoprecipitation Assay

ChIP assay was performed using the ChIP kit (Upstate-Millipore, Billerica, Mass., USA) according to manufacturer's protocol. In brief, PACs from GMP (2.5×10$^6$) cells were isolated from WT mice and treated with or without TGF-b1 (1 ng/mL) for 7 days. Cells were then fixed with 1% formaldehyde, and chromatin was fragmented by sonication. Sheared chromatin was pre-cleared with salmon sperm DNA/protein A agarose and immunoprecipitated with 5 µg control IgG or anti-KLF10 antibody at 4° C. overnight. The antibody/histone complex was collected by the incubation with salmon sperm DNA/protein A agarose at 4° C. for 2 h. To reverse the histone-DNA crosslinks, precipitates were heated at 65° C. overnight. DNA was recovered and purified by phenol/chloroform extraction and ethanol precipitation. qPCR primers for mVEGFR2 promoter were 5'-GGGGCA-GCAAGTGTCTCAG-3' (upper; SEQ ID NO:5) and 5'-TACTCTCTTGGGGTCCTGA-3' (lower; SEQ ID NO:6), located at −294 bp and −30 bp from the transcriptional start site (GenBank Accession No. NT_039306.8).

ELISA

The supernatants from cultured CMPs, GMPs, MEPs and HSCs were collected and subjected to for ELISA using the SearchLight multiplex protein arrays (Aushon Biosystems, Billerica, Mass., USA).

Intracellular Staining of KLF10 in Human PACs

Peripheral blood samples (20 mL) were obtained from healthy subjects and patients with peripheral artery disease, diabetes, and stent thrombosis in accordance with approval by Investigation Review Boards at Brigham and Women's Hospital (Boston, Mass., USA) and Rabin Medical Center (Petah Tikva, Israel). Peripheral blood mononuclear cells were isolated by Ficoll-Paque centrifugation as previously described (Boon et al., Eur Heart J. 2010). Intracellular staining for KLF10 expression in CD34$^+$/VEGFR2$^+$ cells was performed by permeabilization and fixation techniques and using a KLF10 polyclonal antibody, as described (Bieker et al., Journal of Biological Chemistry. 2001, 276: 34355-34358).

Statistical Analysis

Values are expressed herein as mean±standard deviation (S.D.). Differences between values were examined using the Student's t-test (two-tailed) and were considered significant at $P<0.05$.

Example 1

TGF-β1 Modulation of PAC Differentiation and Function

Figure 1B:
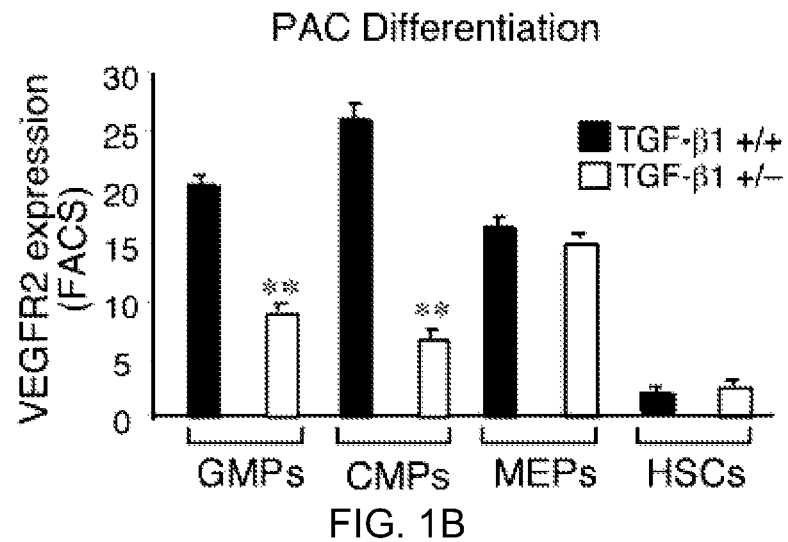
Figure 1C:
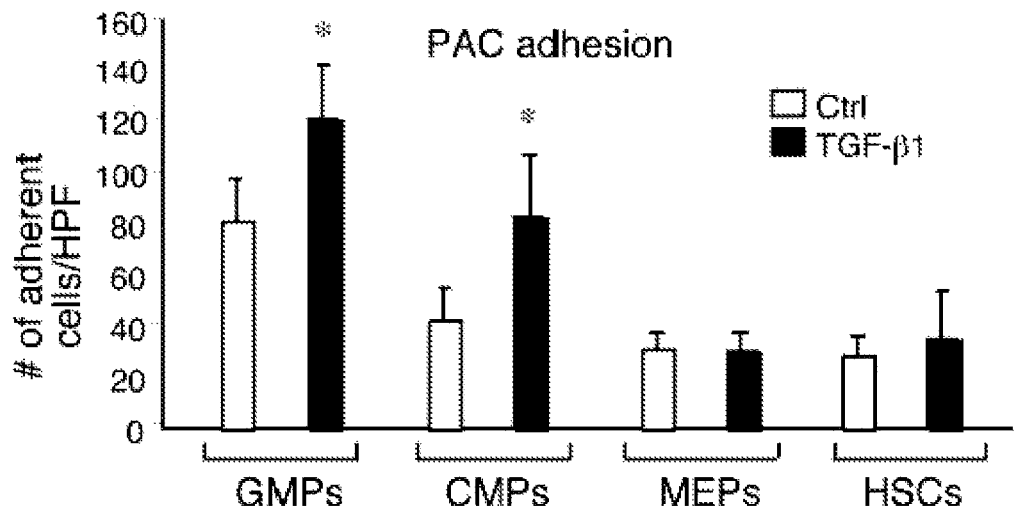
Figure 1D:
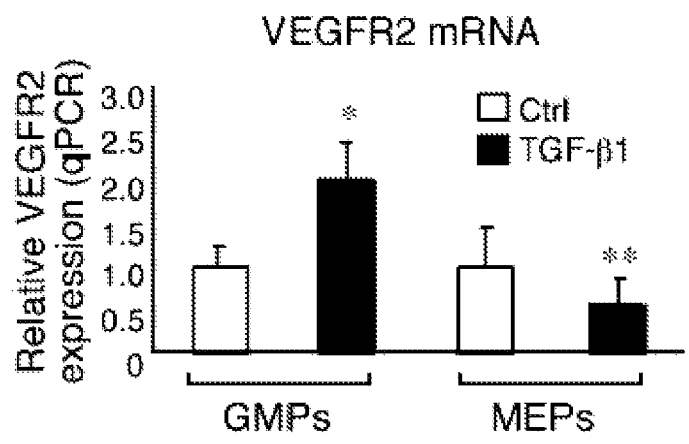
Figure 1E:
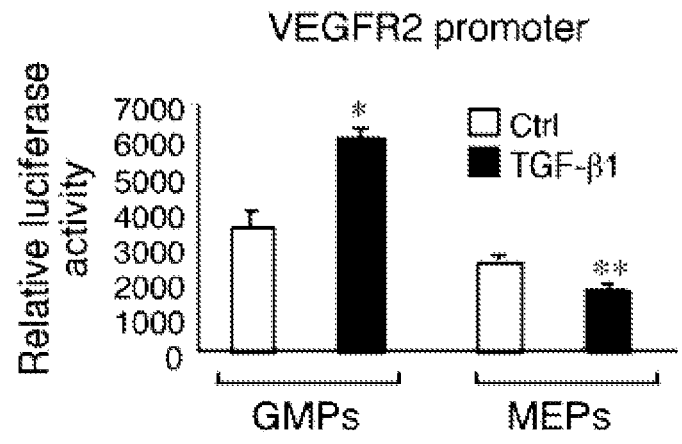
Figure 1F:
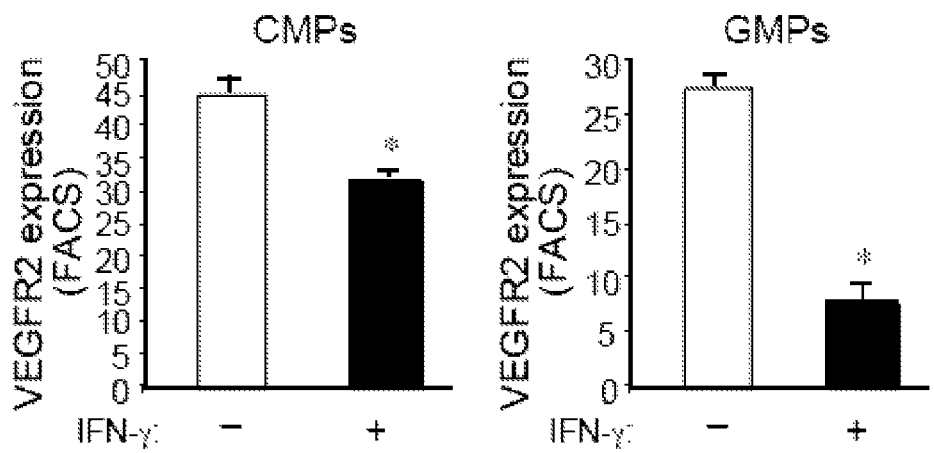

Previous observations suggested that CMPs and GMPs, as opposed to MEPs, HSCs, or CLPs, preferentially differentiated into PACs and exhibited high angiogenic activity in vivo. Signals emanating from TGF-β and IFN-γ are known to antagonize normal cell growth and differentiation events and have been implicated in regulating different aspects of angiogenesis (Ulloa et al., Nature. 1999, 397:710-713; Ghosh et al., J Biol Chem. 2001, 276:11041-11048; Kommineni et al., Biochemical & Biophysical Research Communications. 2008, 374:479-484). To assess the effect of TGF-β1 signaling on PAC differentiation, bone marrow progenitor-derived PACs were cultured for 7 days in the presence or absence recombinant TGF-β1; modulation of the PAC marker VEGFR2 was then examined. As demonstrated in FIG. 1A, treatment of CMP- and GMP-derived progenitors with TGF-β1 resulted in enhanced PAC differentiation by ~28% and ~35%, respectively, as measured by VEGFR2 cell surface expression. To examine the role of IFN-γ on PAC differentiation, bone marrow-derived progenitors were treated in the presence or absence of recombinant IFN-γ in an analogous manner. PAC differentiation was markedly impaired from CMP- and GMP-derived progenitors in the presence of IFN-γ (~31% and 74%, respectively; FIG. 1F). To further verify the role of TGF-β1 on PAC formation, bone marrow progenitors were isolated from TGF-β1 heterozygous/Rag2 knockout mice and their ability to differentiate into PACs was assessed. As demonstrated in FIG. 1B, CMP- and GMP-derived progenitors exhibited marked defects (~73% and 60%, respectively) in their ability to differentiate into PACs, whereas the MEPs from these mice were only minimally impaired. Furthermore, the effect of TGF-β1 on PAC adhesion capacity of the various bone marrow-derived progenitors was explored. Progenitors were cultured in the presence or absence of TGF-β1 and examined for their ability to adhere to fibronectin-coated plates. While TGF-β1 was able to promote CMP- and GMP-derived PACs adherence, no effect of TGF-β1 on MEPs or HSCs was observed (FIG. 1C). Collectively, these observations revealed that PAC differentiation from bone marrow-derived progenitors can be regulated in response to antagonistic signaling pathways. Furthermore, these findings suggested that TGF-β1 signaling may be critically involved in the generation of the pro-angiogenic CMP- and GMP-derived PACs.

The ability of TGF-β1 to effectively promote PAC differentiation through regulation of VEGFR2 gene expression was assessed by investigating the transcript levels and promoter activity. As shown in FIG. 1D, exposure to TGF-β1 led to a ~2-fold increase in VEGFR2 mRNA expression in GMP-derived PACs, whereas there was no effect detectable in MEP-derived PACs. To assess if TGF-β1 could directly mediate the activity of the VEGFR2 promoter, transient transfection reporter studies were performed in bone marrow progenitor-derived PACs. As shown in FIG. 1E, TGF-β1 treatment of GMP-derived PACs led to increased (~43%) VEGFR2 promoter activity. In contrast, VEGFR2 promoter activity was reduced by ~28% in MEP-derived PACs. Taken together, these findings suggested that TGF-β1 may promote PAC differentiation from GMP-derived PACs, in part, by increasing VEGFR2 gene expression.

Example 2

KLF10 Expression and TGF-β1 Responsiveness in PACs

Figure 2A:
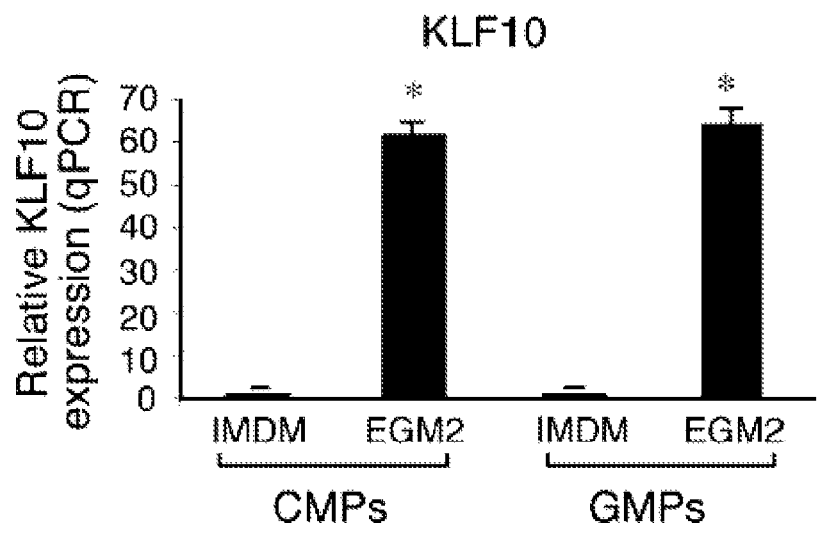
FIGS. 2A-J. Identification of KLF10 expression in PACs and responsiveness to TGF-b1. (A-B) Bone marrow-derived progenitors grown in either hematopoietic IMDM medium or EGM-2 were harvested and expression of Klf10 was examined by qPCR (A) or Western blot analysis (B). *P<0.01. β-actin was used as an internal loading control. (C-D) Bone marrow-derived progenitors grown in EGM-2 medium in the presence or absence of TGF-b1. Klf10 mRNA expression was examined in GMP-derived PACs by qPCR (C). *P<0.01 vs. no TGF-b1. (D) VEGFR2 expression was examined by flow cytometry for the indicated WT or KLF10$^{-/-}$ PACs (n=3 per group); * P<0.01 vs. WT. (E-F) Bone marrow-derived progenitors were transduced with retrovirus GFP-RV-EV (ctrl) or GFP-RV-KLF10. The percentage of GFP$^+$ cells that also expressed VEGFR2 in WT CMP-, GMP-, and HSC-derived PACs (E) or TGF-b1$^{+/+}$ and TGF-b1$^{+/-}$ CMP-derived PACs (F) was assessed by FACS. *P<0.01 vs. EV; **P<0.05 vs. EV TGF-b1$^{+/+}$. (G) ChIP analysis of KLF10 binding to the VEGFR2 promoter in GMP-derived PACs. IgG was used as a non-specific control. Assays were performed in triplicate by real-time qPCR using primers at −294 bp and −30 bp of the VEGFR2 promoter. Values are presented as relative to DNA input. *P<0.01 vs. without TGF-b1 treatment. (H-I) Expression of apoptosis markers Annexin V and caspase 3/7 and cell cycle analyses in WT and KLF10−/− PACs. The indicated bone marrow-derived WT or KLF10−/− CMP-PACs and GMP-PACs were assayed for (H) cell surface expression of Annexin V or Caspase 3/7 by FACS. (n=3 per group) or (I) cell cycle analyses by PI staining and FACS. * P<0.05 vs. WT. (J) Conditioned medium from the indicated bone marrow-derived PACS were added to HUVEC confluent monolayers that contained a scratch induced by pipette tip. The distance that the wound 'closed' after 24 hrs is expressed as percent of wound remaining (n=6 per group). *P<0.01 vs. WT.
Figure 2B:
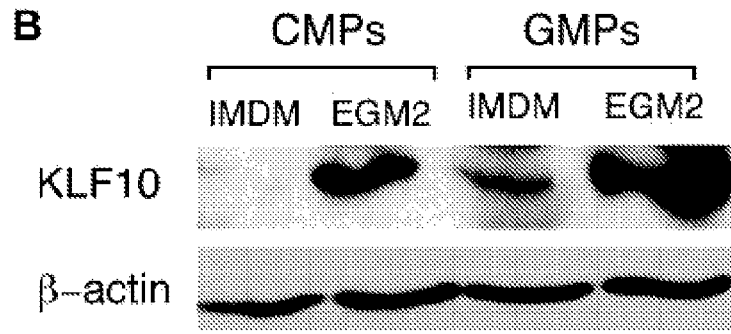
Figure 2C:
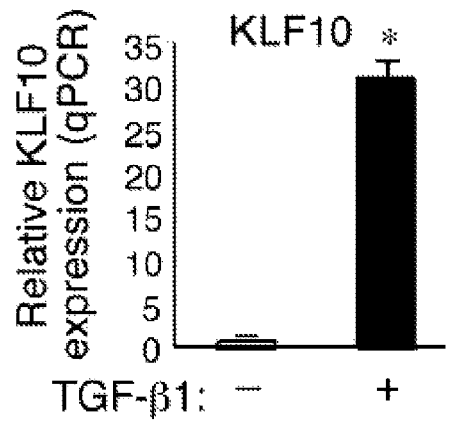
Figure 2D:
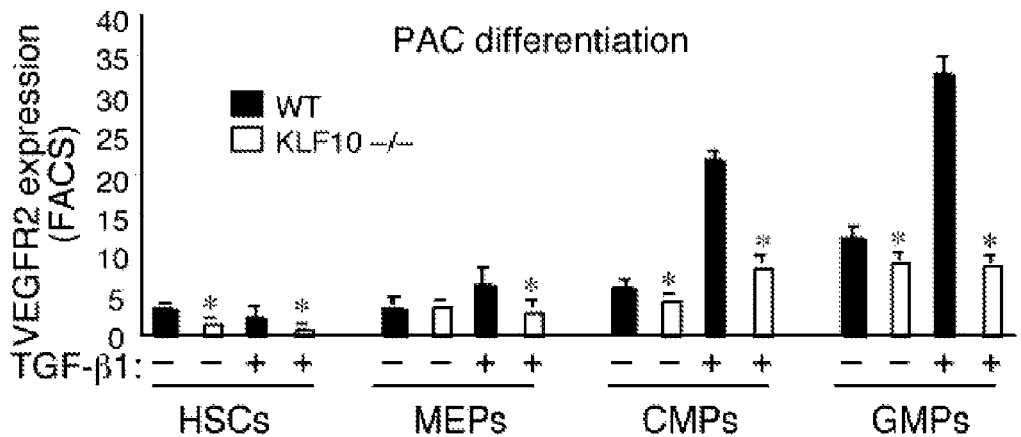
Figure 2E:
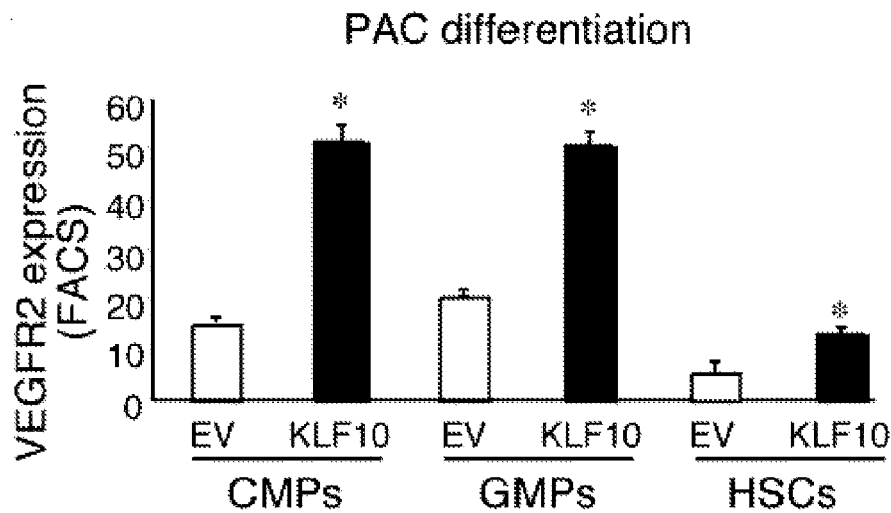
Figure 2F:
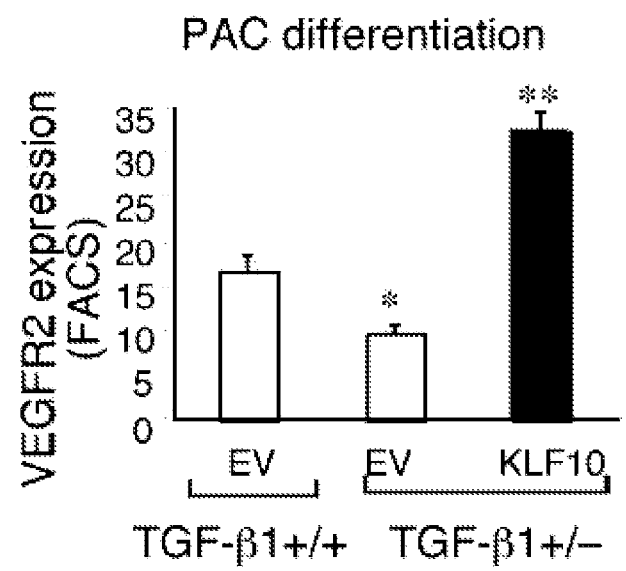
Figure 2G:
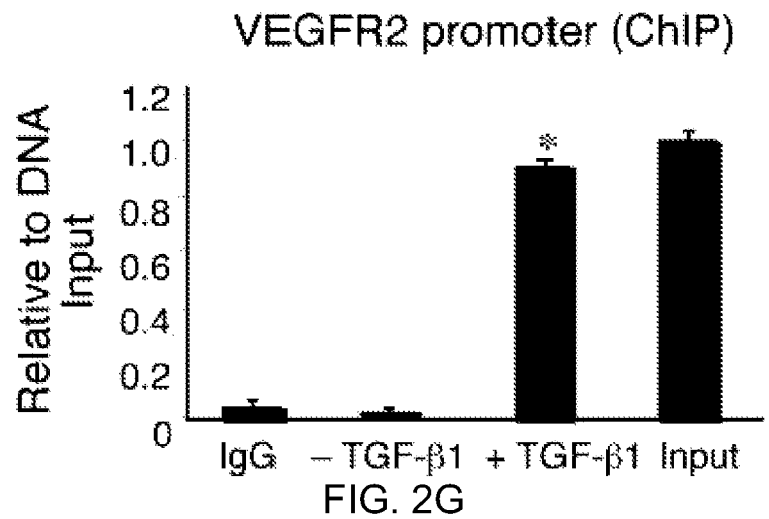
Figure 2H:
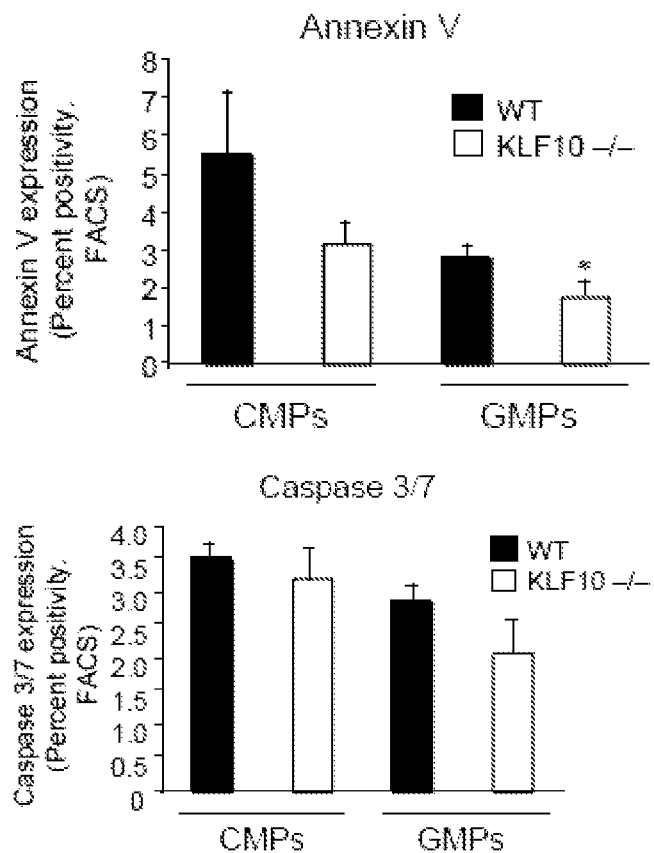
Figure 2I:
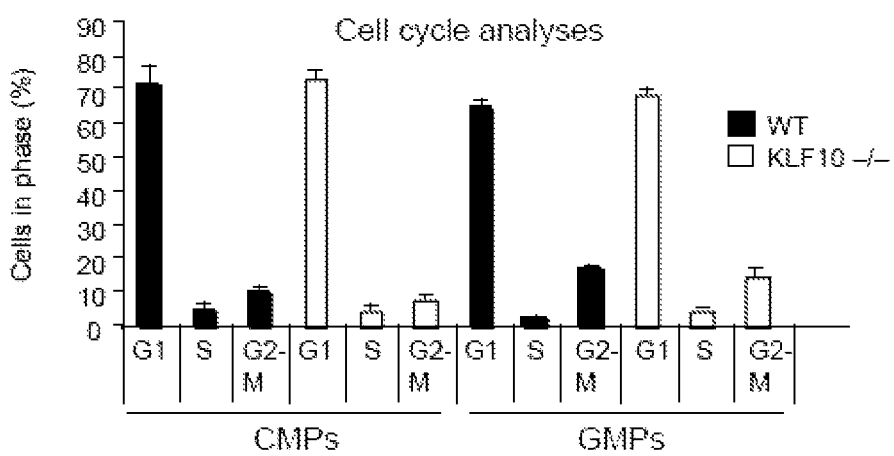

Taking into consideration the acknowledged role for Krüppel-like factors (KLFs) in other hematopoeitic cell types, it was hypothesized that members of this family may also play a role in PAC biology. Using real-time PCR, expression levels of known KLFs (KLF1-17) were screened in freshly isolated CMPs and GMPs and PACs grown in culture from either CMPs or GMPs. Only one KLF member, KLF10, was robustly expressed (~60-fold) in fully-differentiated PACs at both the mRNA and protein level as compared to CMPs or GMPs grown in hematopoietic IMDM medium (FIGS. 2A and B). In contrast, all the other KLFs were found to be minimally expressed, reduced, or unchanged (data not shown). Recent studies by others have demonstrated that KLF10, also known as the Transforming growth factor-Inducible Early Gene-1 (TIEG1), is a TGF-β1 responsive factor in several cell types (Subramaniam et al., J Cell Biochem. 2007, 102:539-548). As shown in FIG. 2C, TGF-β1 treatment potently increased KLF10 expression in GMP-derived PACs (~32-fold). Importantly, KLF10$^{-/-}$ bone marrow GMP and CMP progenitors were significantly impaired in their ability to differentiate into PACs at baseline (~21% and ~6%, respectively) and exhibited a near complete absence of TGF-β1 responsiveness as measured by VEGFR2 cell surface expression (FIG. 2D). In addition, the defect of differentiation in KLF10$^{-/-}$ PACs was not accompanied by an increase of apoptosis as measured by Annexin V and Caspase 3/7 expression (FIG. 2H) or senescence as measured by cell cycle analyses (FIG. 2I). To assess the ability of KLF10 to promote PAC differentiation, overexpression studies using were performed a retrovirus transduction system. VEGFR2 cell surface expression was increased by over 3-fold in CMPs and GMPs overexpressing KLF10 (FIG. 2E). In addition, VEGFR2 expression was also induced by ~2 fold in KLF10-overexpressing HSCs (FIG. 2E), which possess reduced angiogenic properties (Wara et al., Blood 2011 Dec. 8; 118(24):6461-4. Epub 2011 Aug. 9). To assess whether the defect in PAC differentiation from TGF-β1$^{+/-}$ GMPs could be rescued by exogenous KLF10, GFP-empty vector (EV) (Ctrl) or KLF10 (GFP-RV-KLF10) were transduced in TGF-β1$^{+/+}$ or TGF-β1$^{+/-}$ GMPs and VEGFR2 expression was measured by FACS. As shown in FIG. 2F, KLF10-overexpressing cells were capable of rescuing VEGFR2 expression in TGF-β1$^{+/-}$ GMPs to levels even higher than that achieved in TGF-β1$^{+/+}$ GMPs transduced with EV Ctrl. Finally, to determine if KLF10 was capable of binding to the VEGFR2 promoter, chromatin immunoprecipitation (ChIP) studies were performed. As shown in FIG. 2G, in response to TGF-β1 treatment, KLF10 bound to a region within the VEGFR2 promoter in which a consensus CACCC KLF site was located. Collectively, these observations suggested that in response to TGF-β1, KLF10 may be a key downstream transcriptional regulator of PAC differentiation and function.

Example 3

Figure 3A:
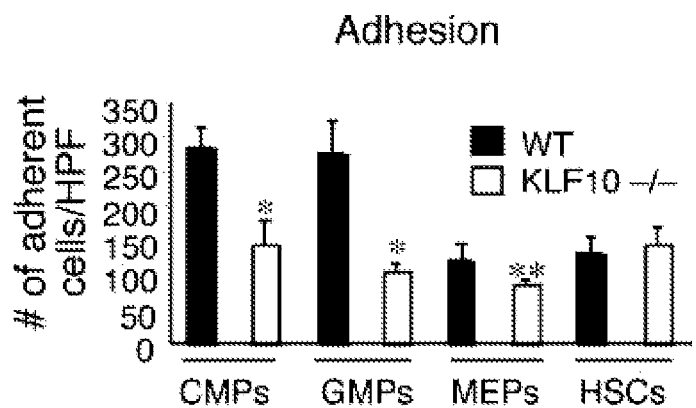
FIGS. 3A-F. KLF10$^{-/-}$ CMP- and GMP-derived PACs possess markedly reduced migratory function and release of soluble paracrine factors. (A) The indicated WT or KLF10$^{-/-}$ bone marrow-derived PACs were assayed for adhesion on fibronectin-coated plates. The number of adherent cells was quantitated after 15 minutes (n=6 per group). *P<0.01 vs. WT; **P<0.05 vs. WT. (B) The indicated WT or KLF10$^{-/-}$ bone marrow-derived PACs were assayed using a modified transwell Boyden chamber in response to serum. The number of cells in the lower chamber was quantitated after 4 hours (n=6 per group). *P<0.01 vs. WT. (C) Cell surface expression of the chemokine receptors CXCR4, CXCR3, and CCR7 was determined on the indicated WT or KLF10$^{-/-}$ bone marrow-derived PACs by flow cytometry and expressed as percent positivity. (D) The indicated WT or KLF10$^{-/-}$ bone marrow-derived PACs were assayed using a modified transwell Boyden chamber in response to 1% BSA control or the chemokines SDF-1a, CXCL10, or CCL21. The number of cells in the lower chamber was quantitated after 4 hours (n=6 per group). *P<0.01 vs. WT; **P<0.05 vs. WT. (E), Culture supernatants were harvested from the indicated WT or KLF10$^{-/-}$ CMP- and GMP-derived PACs assessed by ELISA for the indicated cytokines, growth factors, or chemokines (n=3 per group). *P<0.01 vs. WT. (F) Adhesion of CMP-PACs and GMP-PACs to fibronectin coated plates in response to β1 or β2 integrin-blocking antibodies. The indicated bone marrow-derived CMP-PACs and GMP-PACs from C57BL/6 mice were assayed for adhesion. Cells were incubated on fibronectin-coated plates in the presence or absence of Ctrl, β1, or β2 integrin-blocking antibodies (Chemicon International, Inc) and the number of adherent cells was quantitated after 15 minutes (n=12 per group). * P<0.05 vs. Ctrl; ** P<0.01 vs. Ctrl.
Figure 3B:
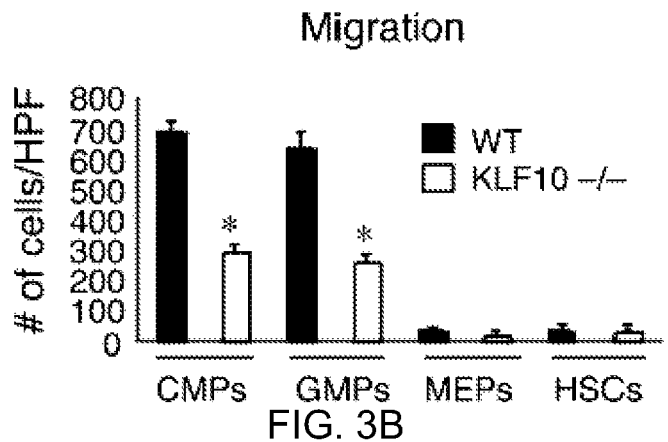
Figure 3C:
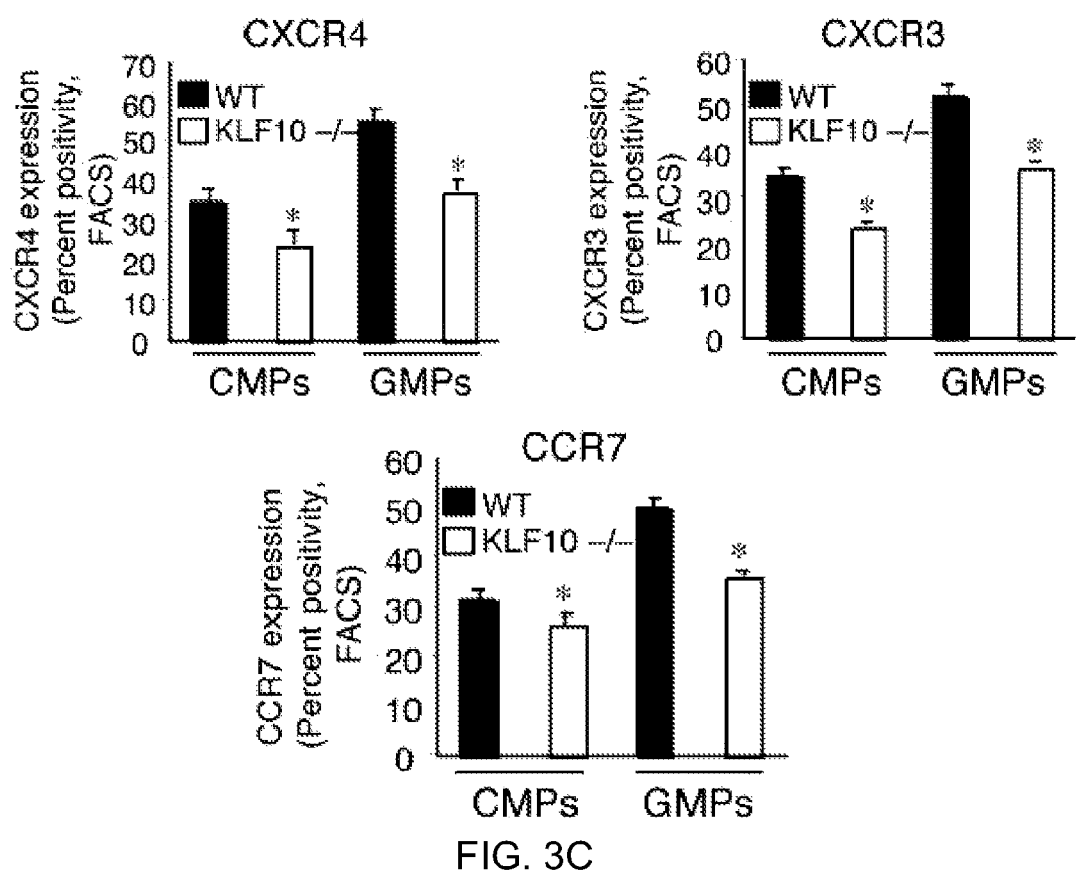
Figure 3D:
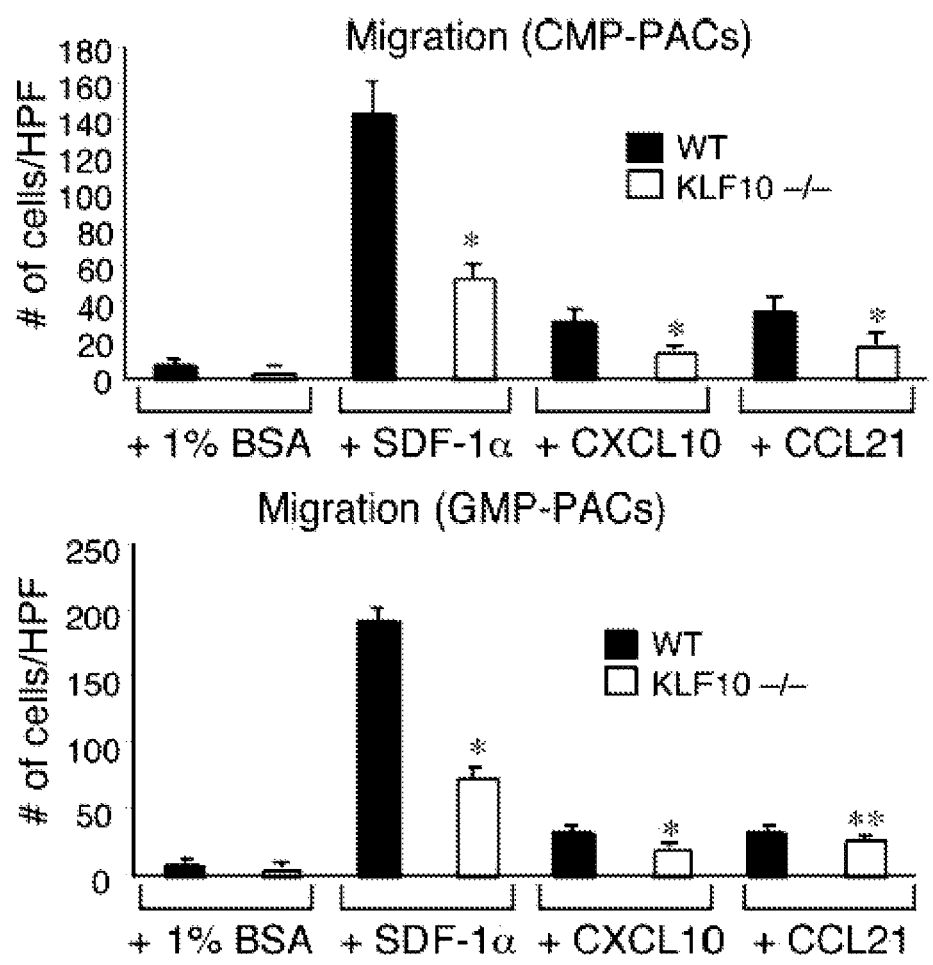
Figure 3E:
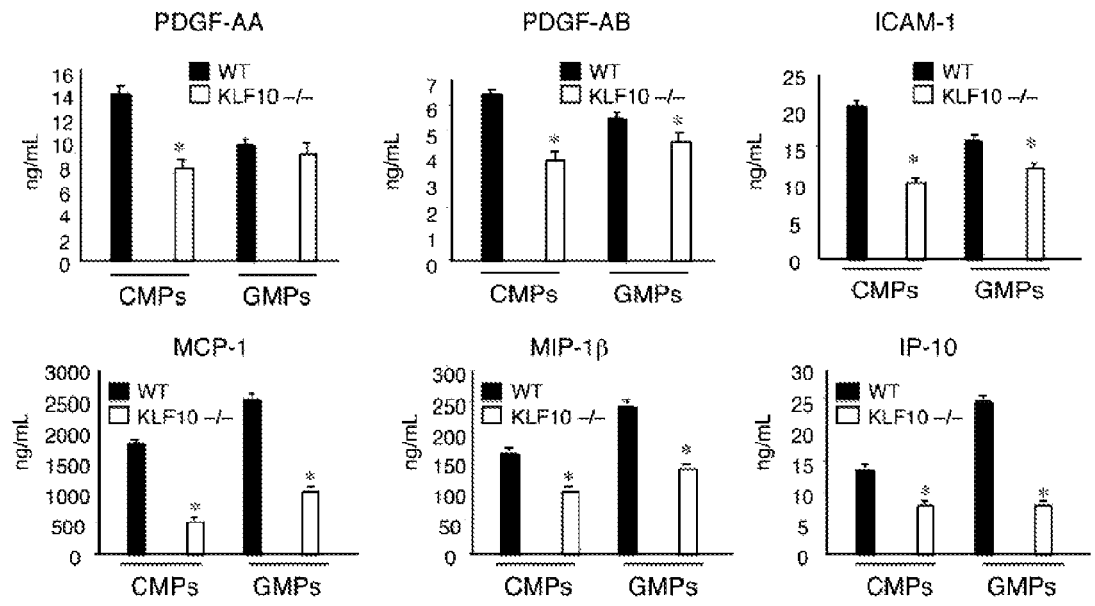
Figure 3F:
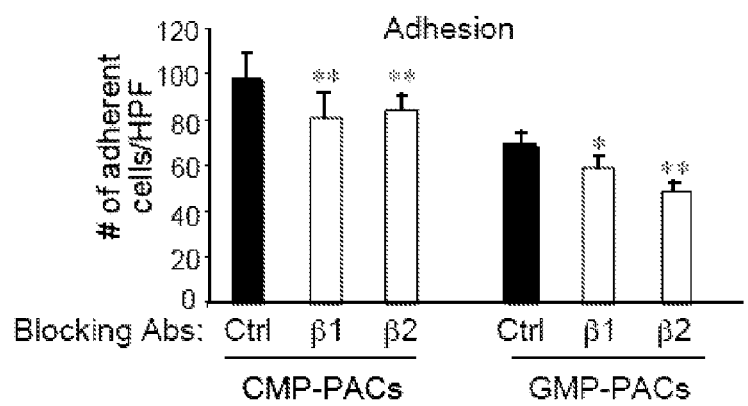

KLF10$^{-/-}$ PACs Possess Markedly Reduced Migratory Function and Release of Soluble Paracrine Factors To explore whether KLF10-deficiency was associated with impaired PAC functional responses, a series of studies were performed to measure effects on cell adhesion, migration, endothelial 'wound healing', as well as the elaboration or expression of cytokines, chemokines, and chemokine receptors. Potentiation of PAC adhesion has been previously shown to ameliorate the development of ischemic injury in animal models (Kawamoto et al., Trends in Cardiovascular Medicine. 2008; 18:33-37). To assess if KLF10$^{-/-}$ PACs have impaired adhesive properties in vitro, equal numbers of bone marrow progenitor-derived PACs from WT or KLF10$^{-/-}$ mice were plated onto fibronectin-coated plates. As shown in FIG. 3A, KLF 10$^{-/-}$ PACs derived from CMPs and GMPs exhibited reduced adherence (by ~48% and ~60%, respectively), as compared to WT CMP- and GMP-derived PACs. In contrast, KLF10$^{-/-}$ PACs derived from HSCs presented no significant differences in adhesion, whereas KLF10$^{-/-}$ MEP-derived PACs showed a more modest reduction (~26%) than WT MEP-derived PACs. To examine the relative contribution of integrin-mediated effects in this assay, WT HSC-, MEP-, CMP-, and GMP-derived PACs were incubated in the presence or absence of integrin blocking antibodies. As shown in FIG. 3F, blocking antibodies to either β1 or β2 integrins had modest effects (~13%-28%) at inhibiting the adherence of WT CMP- or GMP-derived PACs to fibronectin-coated plates. These data suggest that integrin-mediated events play a minor role in CMP- or GMP-derived PAC adhesion.

PACs promote angiogenesis in response to injury through several mechanisms including adhesion and subsequent transmigration. To explore migratory function in detail, various PACs were placed in the top of a transwell Boyden chamber and assessed for their ability to translocate to the lower chamber in response to serum (FIG. 3B) or to chemokines implicated in neovascularization (FIG. 3D). The KLF10$^{-/-}$ PACs derived from CMPs and GMPs were markedly impaired in their ability to transmigrate in response to serum (FIG. 3B); these cells migrated ~57% and ~58% less than their respective WT PACs (FIG. 3B). In contrast, those KLF10$^{-/-}$ PACs derived from MEPs and HSCs showed no differences in their ability to transmigrate as compared to their WT PAC counterparts. Next, the expression of chemokine receptors implicated in neovascularization KLF10$^{-/-}$ CMP- and GMP-derived PACs was examined. As compared to WT CMP- and GMP-derived PACs, KLF10$^{-/-}$ PACs exhibited reduced cell surface expression of the chemokine receptors CXCR4, CXCR3, and CCR7 (FIG. 3C). The relative ability of CMP- and GMP-derived PACs to migrate in response to the chemokines SDF-1α (ligand for CXCR4), CXCL10 (ligand for CXCR3), and CCL21 (ligand for CCR7) was further assessed. As shown in FIG. 3D, migration was significantly reduced by over 60% in response to the chemokine SDF-1α for both KLF10$^{-/-}$ CMP- and GMP-derived pro-angiogenic cells as compared to their WT counterparts. Furthermore, among WT CMP- and GMP-derived PACs, SDF-1α produced a more potent migratory response compared to the chemokines CXCL10 and CCL21. Specifically, SDF-1α increased migration by 19-fold and 23-fold higher compared to BSA-controls in WT GMP- and CMP-derived PACs, whereas CXCL10 and CCL21 increased migration by only 4-fold. Finally, migration was reduced more modestly in response to the chemokines CXCL10 and CCL21 in KLF10$^{-/-}$ pro-angiogenic cells, an effect underscoring that the SDF-1α/CXCR4 axis is one of the dominant migratory defects exhibited by KLF10$^{-/-}$ CMP- and GMP-derived pro-angiogenic cells.

Figure 2J:
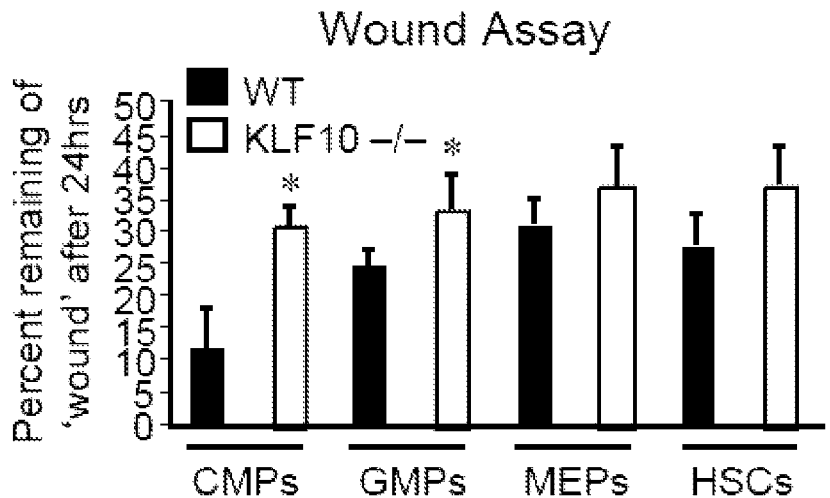

PACs can elaborate a variety of pro-angiogenic cytokines, growth factors, and chemokines. To assess the ability of KLF10$^{-/-}$ PACs to elaborate such factors, the classic in vitro endothelial 'wound assay' (scratch method by a pipette tip) was performed using the conditioned medium from WT and KLF10$^{-/-}$ PACs. The ability of HUVECs to 'close' over the wound within 24 hours demonstrated that conditioned medium harvested from KLF10$^{-/-}$ PACs derived from CMPs and GMPs was impaired in its ability to promote 'wound healing' by ~57% and ~26%, respectively, as compared to WT PACs (FIG. 2J); in contrast, no differences were observed between conditioned medium collected from WT or KLF10$^{-/-}$ for either MEP- or HSC-derived PACs. Finally, to explore which factors normally secreted from CMP- or GMP-derived PACs may be reduced as a result of KLF10 deficiency, the conditioned medium was analyzed by ELISA. As shown in FIG. 3E, KLF10$^{-/-}$ PACs were unable to elaborate many of the growth factors, cytokines, and chemokines investigated. In particular, conditioned medium from CMP-derived KLF10$^{-/-}$ PACs was found to have strikingly reduced levels of PDGF-AA and PDGF-AB (~39% and ~44%, respectively), as compared to WT CMP-derived PACs. In contrast, PDGF-AB secreted from GMP-derived KLF10$^{-/-}$ PACs was reduced to a lesser extent (~18%) and PDGF-AA secretion was only slightly different from WT. Other factors such as ICAM-1 and the chemokines MCP-1, MIP-1β, and IP-10 were potently reduced in both CMP- and GMP-derived KLF10$^{-/-}$ PACs, as compared to their WT counterparts (FIG. 3E). Collectively, these findings indicated that KLF10$^{-/-}$ CMP- and GMP-derived PACs possess major functional defects in their ability to migrate, specifically in response to SDF-1α, and in their ability to release several soluble paracrine factors implicated in promoting angiogenesis.

Example 4

Figure 4A:
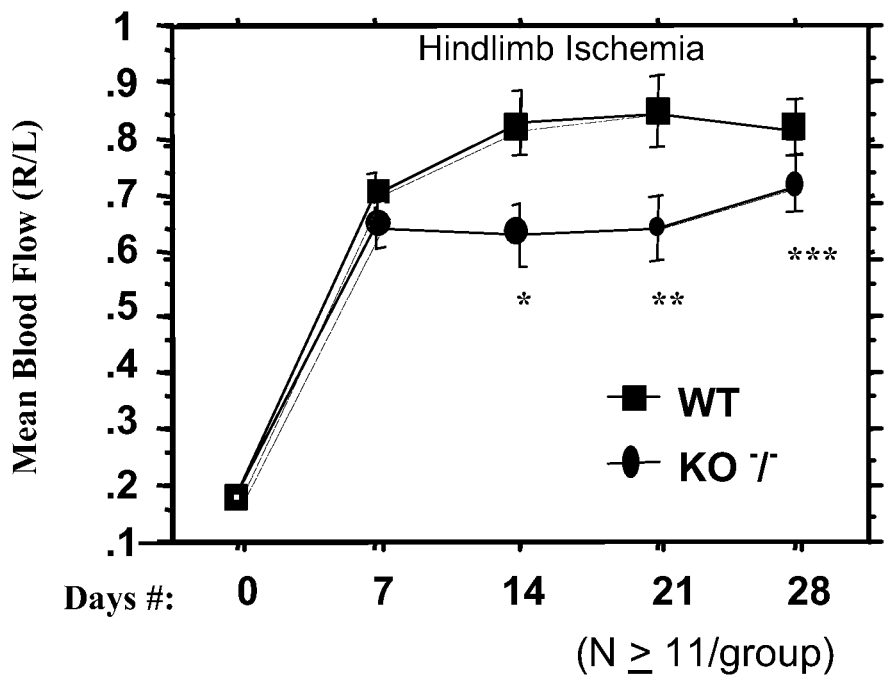
FIGS. 4A-F. Effect of KLF10 deficiency on hindlimb ischemia. WT or KLF10$^{-/-}$ mice underwent femoral artery ligation to induce hindlimb ischemia. KLF10$^{-/-}$ mice (n=2 of 21) developed auto-amputation of the ischemic leg. (A) Quantitation of blood flow recovery for each time point over 28 days was calculated as the mean blood flow (right (ischemic) leg)/left (non-ischemic) leg) by laser Doppler imaging (785 nm near-infrared Laser Doppler Imager-2, Moor Instruments).*P<0.01 vs. WT; **P<0.05 vs. WT. (B) FACS analyses of circulating PACs (Sca-1$^+$/VEGFR2$^+$) in WT or KLF10$^{-/-}$ mice 7 days after femoral artery ligation (n=9-10 per group). *P<0.05 vs. WT. (C) WT or KLF10$^{-/-}$ PACs (1:1 mix of CMP- and GMP-derived PACs) were intramuscularly injected immediately after femoral artery ligation in KLF10$^{-/-}$ mice. Mean blood flow recovery (ischemic leg/non-ischemic leg) was measured by laser Doppler imaging after 3 days. *P<0.05 vs. WT+PBS. (D-E) Frozen sections of quadriceps muscles harvested 3 days after i.m. injection of WT or KLF10$^{-/-}$ PACs were labeled with cell tracker and a FITC-conjugated mAb to CD31. In (D), sections were analyzed for CD31 staining using an AQUA/PM2000 Imaging Platform (HistoRx) and automated quantitative analysis was performed using Software suite version 2.2 (HistoRx). *P<0.01 vs. WT; n=4 mice per group. In (E), sections were examined using an Olympus, Fluoview, Model FV1000 camera at 10× magnification and FV10-ASW Software version 02.01 to determine the percent of labeled PACs that co-localized with CD31-positive cells. * P<0.01 vs. WT; n=4 mice per group. (F) Immunohistochemistry of caspase-3 expression in adductor muscles of KLF10-/- mice injected i.m. with WT or KLF10-/- PACs. Caspase-3 expression was examined as a marker of apoptosis. Graph represents mean data from n=5 per group; * P<0.01. Images were visualized with an Olympus, Model Bx43 microscope and Qcapture software version 2.68.6.
Figure 4B:
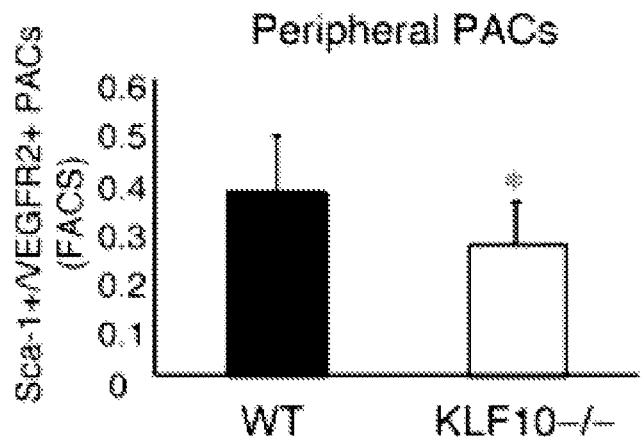
Figure 4C:
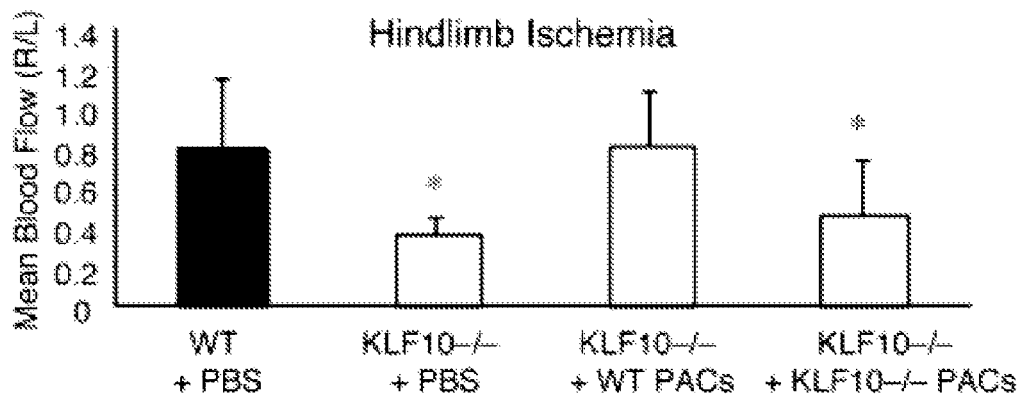
Figure 4D:
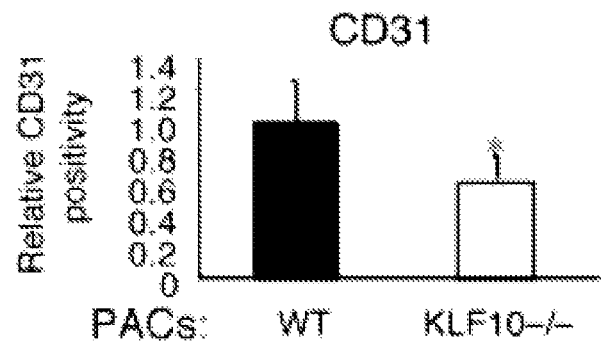
Figure 4E:
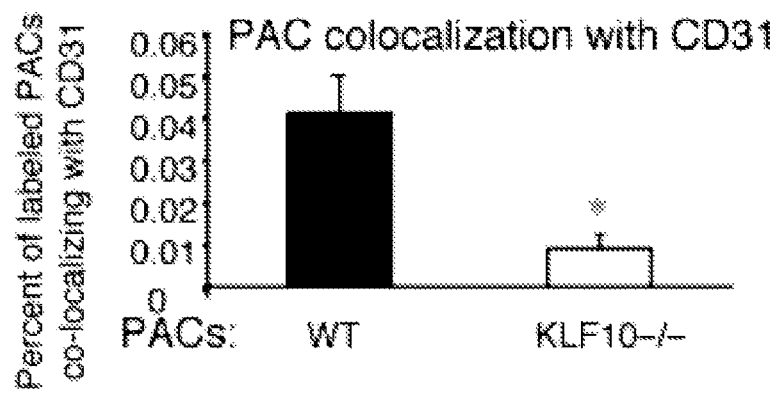
Figure 4F:
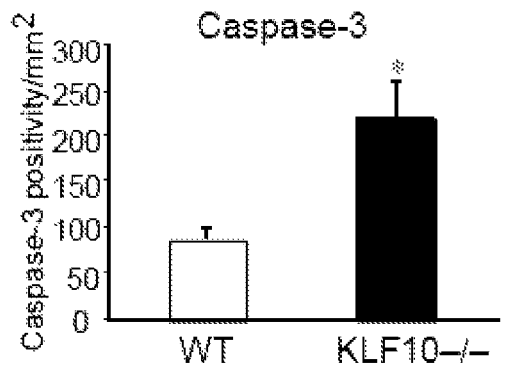

KLF10–/– Mice Develop Markedly Impaired Blood Flow Recovery Associated with Reduced Levels of Peripheral Blood PACs and Neovascularization in Response to Hindlimb Ischemia To examine if the impaired differentiation responses in KLF10$^{-/-}$ PACs in vitro correlated to defects in an in vivo mouse model of neovascularization, hindlimb ischemia studies were performed by femoral artery ligation. Approximately 7-14 days after femoral artery ligation, KLF10$^{-/-}$ mice developed either auto-amputation of the ischemic leg (n=2 of 21 KLF10$^{-/-}$ mice vs. 0 of 21 WT mice) or severely impaired blood flow recovery responses as measured by laser Doppler imaging (FIG. 4A). Quantitation performed at days 14, 21, and 28 post-ligature surgery revealed significantly reduced blood flow recovery (23%, 24%, and 12%, respectively), in KLF10$^{-/-}$ mice compared to WT mice. Measurement of peripheral blood PACs at day 7 post-ligation surgery demonstrated that KLF10$^{-/-}$ mice had significantly decreased amounts of mobilized peripheral blood PACs, ~38% lower than WT mice (FIG. 4B). To assess the relative contribution of WT and KLF10$^{-/-}$ PACs in their ability to rescue the defect in blood flow recovery in KLF10$^{-/-}$ mice, i.m. injections were performed at the time of femoral artery ligation. While WT PACs (derived from equal portions of CMPs and GMPs) were able to completely rescue blood flow recovery in KLF10$^{-/-}$ mice, KLF10$^{-/-}$ PACs (also derived equally from CMPs and GMPs) had no effect (FIG. 4C). Furthermore, immunofluorescence staining for the platelet endothelial cell adhesion molecule CD31 indicated markedly reduced neovascularization in quadriceps muscles after i.m. injections with KLF10$^{-/-}$ PACs, as opposed to that seen in quadriceps muscles injected with WT PACs (FIG. 4D). Quadriceps muscles injected with KLF10$^{-/-}$ PACs also demonstrated higher caspase-3 levels when evaluated by immunostaining, suggesting that KLF10$^{-/-}$ PACs may not be able to protect against injury-induced apoptosis (FIG. 4F). Finally, despite the fact that the WT PACs were capable of incorporating into capillary structures, albeit at extremely low frequencies, there was no evidence of similar incorporation by the KLF10$^{-/-}$ PACs (FIG. 4E). Taken together, these observations highlight that KLF10$^{-/-}$ mice have markedly reduced blood flow recovery, an effect that can be rescued by WT PACs, but not KLF10$^{-/-}$ PACs.

Figure 5A:
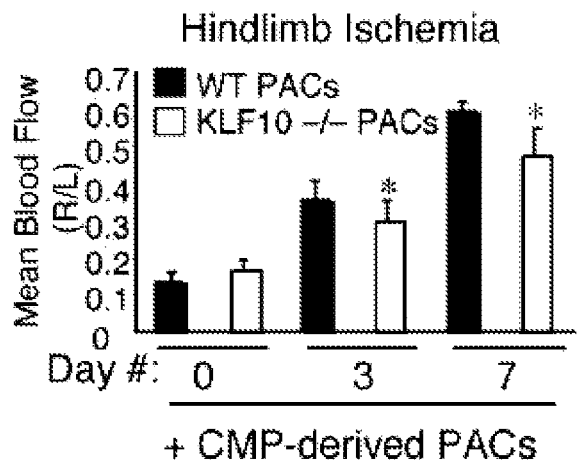
FIGS. 5A-D. Effect of KLF10$^{-/-}$ PACs on blood flow recovery in WT mice. (A-D) WT mice underwent femoral artery ligation to induce hindlimb ischemia. WT or KLF10$^{-/-}$ CMP-, GMP-, MEP-, or HSC-derived PACs were intramuscularly injected immediately after femoral artery ligation (n=5 per group). Mean blood flow recovery (ischemic leg/non-ischemic leg) was measured by tissue Doppler imaging. *P<0.05 vs. WT PACs.
Figure 5B:
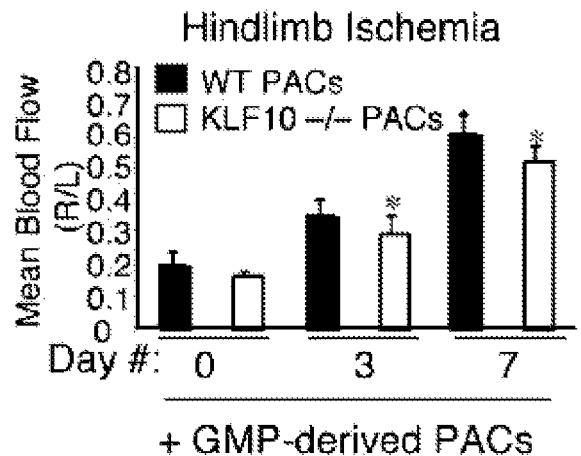
Figure 5C:
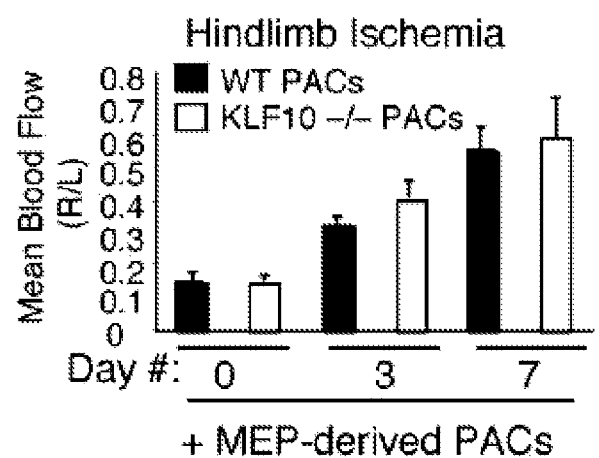
Figure 5D:
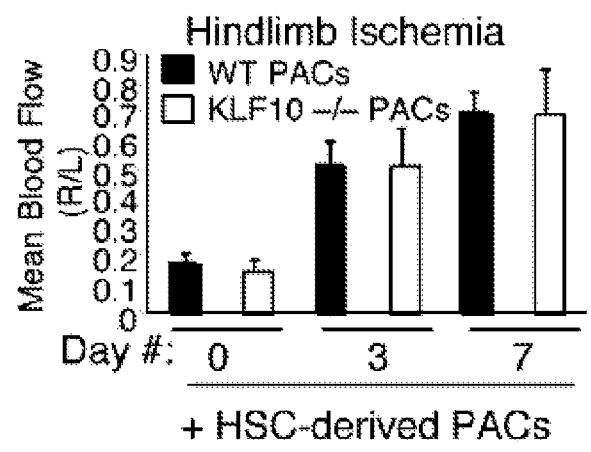
Figure 6:
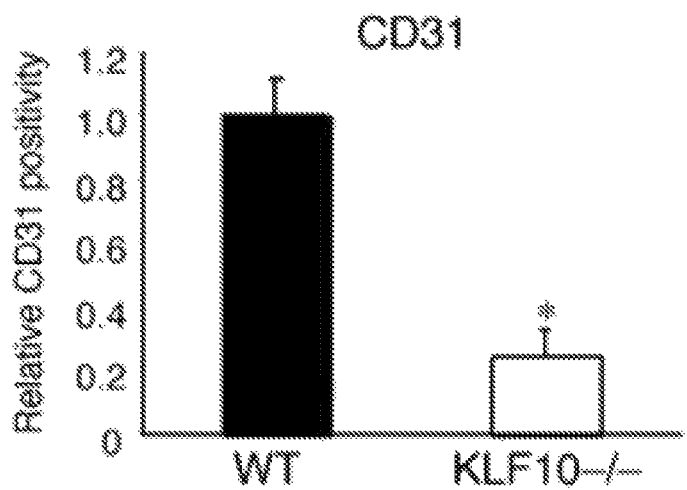
FIG. 6. Reduced angiogenesis in Matrigel plugs implanted in KLF10$^{-/-}$ mice. Matrigel plugs subcutaneously implanted for 8 days in WT or KLF10$^{-/-}$ mice (n=10 per group) were stained for CD31. Angiogenesis in whole Matrigel plugs. Matrigel images were photographed using an Olympus, Model SZ61 camera. CD31 staining in paraffin sections (5 μm) was analyzed using an Olympus, Fluoview, Model FV1000 camera at 10× magnification and FV10-ASW Software version 02.01 and quantitated as relative CD31 positivity. *P<0.01 vs. WT.

To verify the effects on blood flow recovery between individual WT and KLF10$^{-/-}$ bone marrow-derived PAC subsets in WT mice, i.m. injections were performed in an analogous manner at the time of femoral artery ligation. As shown in FIGS. 5A-D, KLF10$^{-/-}$ CMP- and GMP-derived PACs had reduced ability to rescue blood flow recovery in WT mice compared to WT CMP- and GMP-derived PACs (FIGS. 5A and B, respectively). In contrast, there were no reductions in blood flow recovery observed after i.m. injections of KLF10$^{-/-}$ MEP- or HSC-derived PACs compared to WT MEP- or HSC-derived PACs (FIGS. 5C and 5D, respectively). Thus, KLF10-deficient CMP- and GMP-derived PACs exhibit significant defects in promoting blood flow recovery in WT mice. These findings further underscore the inability of KLF10$^{-/-}$ CMP- and GMP-derived PACs to promote neovascularization either directly by incorporation into capillaries or indirectly by paracrine-mediated effects.

Example 5

Reduced Angiogenesis in Matrigel Plugs from KLF10$^{-/-}$ Mice

The Matrigel plug assay is a well-established model of angiogenesis in vivo.[24] To determine whether KLF10$^{-/-}$ mice develop fewer capillaries than their WT counterparts, Matrigel plug implantation studies were performed. Upon explanation, Matrigel plugs from KLF10$^{-/-}$ mice were found to be markedly less red in appearance and to have ~75% less angiogenesis than plugs from WT mice by CD31 staining. These findings further demonstrated that KLF10$^{-/-}$ mice possess marked in vivo defects in neovascularization.

Example 6

Figure 7A:
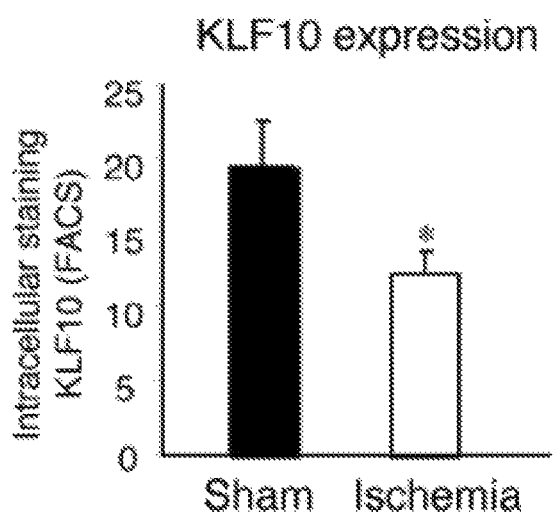
FIGS. 7A-C. KLF10 expression in response to hindlimb ischemia in mice and in human patients with PAD. (A) 8-10 week old, male WT mice underwent femoral artery ligation to induce hindlimb ischemia (ischemia) or sham control operation (sham) and expression of Klf10 was determined by intracellular staining of circulating PACs (Sca1$^+$/VEGFR2$^+$) after 7 days by flow cytometry. *P<0.01 vs. Sham. (B) Expression of KLF10 was determined in circulating PACs (CD34$^+$/VEGFR2$^+$) obtained from healthy control subjects or patients with symptomatic peripheral artery disease (PAD). *P<0.01 vs. healthy controls. (C) Association of KLF10 expression in healthy subjects or in patients with diabetes or stent thrombosis. Percent expression of KLF10 was determined by intracellular staining by flow cytometry of circulating PACs (CD34$^+$/VEGFR2$^+$) obtained from healthy control subjects or patients with diabetes or stent thrombosis. * P<0.01 vs. healthy controls.
Figure 7B:
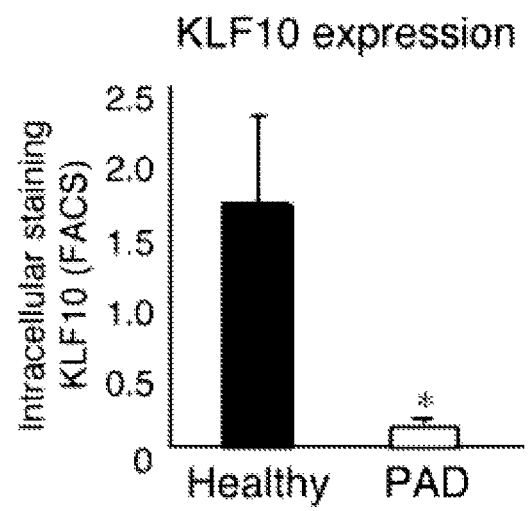
Figure 7C:
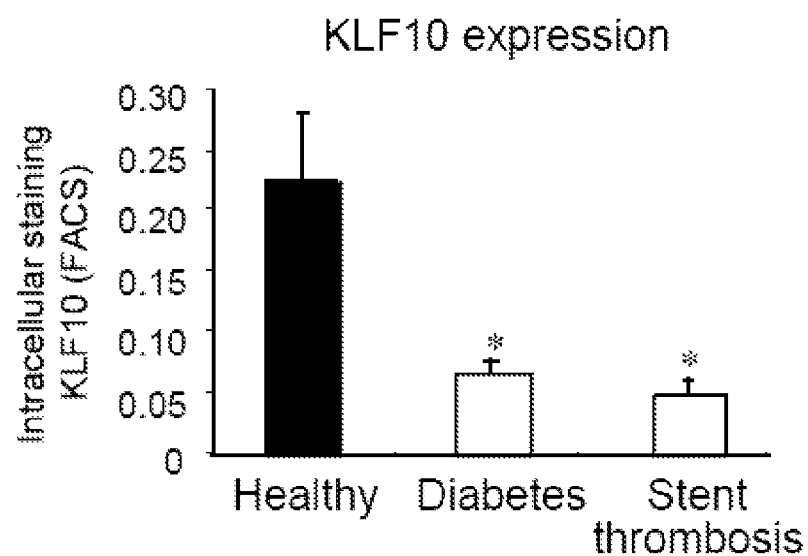

KLF10 Expression During Hindlimb Ischemia in Mice and in Humans with Peripheral Artery Disease Several studies have identified an association with reduced PAC levels or function in patients with ischemic disease states such as PAD (Fadini et al., Arterioscler Thromb Vasc Biol. 2006, 26:2140-2146; Vasa et al., Circ Res. 2001, 89:E1-7; Hill et al., [see comment] [reprint in Can J. Cardiol. 2004 August; 20 Suppl B:44B-48B; PMID:

15309205]. New England Journal of Medicine. 2003, 348: 593-600). Since the findings thus far had suggested that KLF 10 expression was important for optimal PAC function, it was hypothesized that KLF10 expression in circulating PACs would be reduced both in mice with hindlimb ischemia as well as in human patients with peripheral artery disease. First, femoral artery ligation studies were performed in mice and the KLF10 expression measured in PACs by intracellular staining and FACS. Compared to circulating PACs from sham-operated control mice, KLF10 levels were significantly reduced (by 34%) in PACs from mice with hindlimb ischemia (FIG. 7A). Reduced expression of KLF10 was also observed in PACs from patients with PAD (91% lower than healthy controls; FIG. 7B). Demographics are shown in Table 1 for healthy subject controls and PAD patients including gender, age, and presence of diabetes. While the PAD patients exhibited higher age (67.8±8.6 vs. 57.3±7.0) compared to the healthy subject control group, there was no correlation of KLF10 expression with increasing age within either group (data not shown). In addition, expression levels of KLF10 were also reduced in patients with disease states known to be associated with PAC dysfunction including diabetes (reduced by 71%) and stent thrombosis (reduced by 78%) (FIG. 7C). Taken together, these findings suggest that reduced KLF10 levels in PACs represent an effective biomarker for the presence of PAD and that TGF-β1/KLF10 signaling is important for optimal PAC function.

TABLE 1

Demographics of healthy subject controls and PAD patients.

| | Patient # | PAD, Symptomatic claudication or ABI* < 0.9 | Sex | Age, years | Diabetes |
|---|---|---|---|---|---|
| Healthy Subject Controls | Patient 1 | No | M | 47 | No |
| | Patient 2 | No | M | 49 | No |
| | Patient 3 | No | F | 51 | Yes |
| | Patient 4 | No | M | 61 | No |
| | Patient 5 | No | M | 64 | No |
| | Patient 6 | No | F | 64 | No |
| | Patient 7 | No | M | 62 | No |
| | Patient 8 | No | M | 60 | No |
| PAD Patients | Patient 9 | Yes | M | 68 | Yes |
| | Patient 10 | Yes | M | 80 | No |
| | Patient 11 | Yes | M | 75 | No |
| | Patient 12 | Yes | F | 80 | No |
| | Patient 13 | Yes | F | 71 | No |
| | Patient 14 | Yes | M | 67 | Yes |
| | Patient 15 | Yes | M | 55 | No |
| | Patient 16 | Yes | M | 73 | No |
| | Patient 17 | Yes | M | 66 | No |
| | Patient 18 | Yes | F | 61 | No |
| | Patient 19 | Yes | M | 63 | No |
| | Patient 20 | Yes | M | 54 | Yes |

*ABI = ankle-brachial index.

REFERENCES

1. Melero-Martin J M, Bischoff J. Chapter 13. An in vivo experimental model for postnatal vasculogenesis. Methods in Enzymology. 2008; 445:303-329.
2. Frontelo P, Manwani D, Galdass M, et al. Novel role for EKLF in megakaryocyte lineage commitment. Blood. 2007; 110:3871-3880.
3. Alder J K, Georgantas R W, 3rd, Hildreth R L, et al. Kruppel-like factor 4 is essential for inflammatory monocyte differentiation in vivo. J. Immunol. 2008; 180:5645-5652.
4. Liao X, Sharma N, Kapadia F, et al. Kruppel-like factor 4 regulates macrophage polarization. J Clin Invest. 2011.
5. van Royen N, Hoefer I, Buschmann I, et al. Exogenous application of transforming growth factor beta 1 stimulates arteriogenesis in the peripheral circulation. FASEB Journal. 2002; 16:432-434.
6. Wahl S M, Hunt D A, Wakefield L M, et al. Transforming growth factor type beta induces monocyte chemotaxis and growth factor production. Proc Natl Acad Sci USA. 1987; 84:5788-5792.
7. Bartolome R A, Sanz-Rodriguez F, Robledo M M, Hidalgo A, Teixido J. Rapid up-regulation of alpha4 integrin-mediated leukocyte adhesion by transforming growth factor-beta1. Mol Biol Cell. 2003; 14:54-66.
8. Nesti L J, Caterson E J, Wang M, et al. TGF-beta1 calcium signaling increases alpha5 integrin expression in osteoblasts. J Orthop Res. 2002; 20:1042-1049.
9. Duan H, Cheng L, Sun X, et al. LFA-1 and VLA-4 involved in human high proliferative potential-endothelial progenitor cells homing to ischemic tissue. Thromb Haemost. 2006; 96:807-815.
10. Mobius-Winkler S, Hollriegel R, Schuler G, Adams V. Endothelial progenitor cells: implications for cardiovascular disease. Cytometry Part A: The Journal of the International Society for Analytical Cytology. 2009; 75:25-37.
11. Hirschi K K, Ingram D A, Yoder M C. Assessing identity, phenotype, and fate of endothelial progenitor cells. Arteriosclerosis, Thrombosis & Vascular Biology. 2008; 28:1584-1595.
12. Bailey A S, Willenbring H, Jiang S, et al. Myeloid lineage progenitors give rise to vascular endothelium. [see comment]. Proceedings of the National Academy of Sciences of the United States of America. 2006; 103:13156-13161.
13. Zhang J, Cao R, Zhang Y, Jia T, Cao Y, Wahlberg E. Differential roles of PDGFR-alpha and PDGFR-beta in angiogenesis and vessel stability. Faseb J. 2009; 23:153-163.
14. Lu H, Xu X, Zhang M, et al. Combinatorial protein therapy of angiogenic and arteriogenic factors remarkably improves collaterogenesis and cardiac function in pigs. Proc Natl Acad Sci USA. 2007; 104:12140-12145.
15. Lindahl P, Johansson B R, Leveen P, Betsholtz C. Pericyte loss and microaneurysm formation in PDGF-B-deficient mice. Science. 1997; 277:242-245.
16. Chavakis E, Dimmeler S. Homing of Progenitor Cells to Ischemic Tissues. Antioxid Redox Signal. 2010.
17. Fujiyama S, Amano K, Uehira K, et al. Bone marrow monocyte lineage cells adhere on injured endothelium in a monocyte chemoattractant protein-1-dependent manner and accelerate reendothelialization as endothelial progenitor cells. Circ Res. 2003; 93:980-989.
18. Chavakis E, Aicher A, Heeschen C, et al. Role of beta2-integrins for homing and neovascularization capacity of endothelial progenitor cells. J Exp Med. 2005; 201:63-72.
19. Derynck R, Akhurst R J. Differentiation plasticity regulated by TGF-beta family proteins in development and disease. Nat Cell Biol. 2007; 9:1000-1004.
20. Heldin C H, Landstrom M, Moustakas A. Mechanism of TGF-beta signaling to growth arrest, apoptosis, and epithelial-mesenchymal transition. Curr Opin Cell Biol. 2009; 21:166-176.
21. Dvorin E L, Wylie-Sears J, Kaushal S, Martin D P, Bischoff J. Quantitative evaluation of endothelial progenitors and cardiac valve endothelial cells: proliferation and differentiation on poly-glycolic acid/poly-4-hydroxybutyrate scaffold in response to vascular endothelial growth factor and transforming growth factor beta1. Tissue Eng. 2003; 9:487-493.

22. Robinson A P, Foraker J E, Ylostalo J, Prockop D J. Human Stem/Progenitor Cells from Bone Marrow Enhance Glial Differentiation of Rat Neural Stem Cells: A Role for Transforming Growth Factor beta and Notch Signaling. Stem Cells Dev. 2010.

23. Poon E, Clermont F, Firpo M T, Akhurst R J. TGFbeta inhibition of yolk-sac-like differentiation of human embryonic stem-cell-derived embryoid bodies illustrates differences between early mouse and human development. J Cell Sci. 2006; 119:759-768.

24. Moonen J R, Krenning G, Brinker M G, Koerts J A, van Luyn M J, Harmsen M C. Endothelial progenitor cells give rise to pro-angiogenic smooth muscle-like progeny. Cardiovasc Res. 2010; 86:506-515.

25. Imamura H, Ohta T, Tsunetoshi K, et al. Transdifferentiation of bone marrow-derived endothelial progenitor cells into the smooth muscle cell lineage mediated by transforming growth factor-beta1. Atherosclerosis. 2010; 211:114-121.

26. Mogi M, Walsh K, Iwai M, Horiuchi M. Akt-FOXO3a signaling affects human endothelial progenitor cell differentiation. Hypertens Res. 2008; 31:153-159.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing and treating peripheral artery disease (PAD) in a subject, the method comprising:
   isolating $CD34^+/VEGFR2^+$ pro-angiogenic peripheral blood cells from the subject by flow cytometry;
   performing an assay to determine a level of Krüppel-like Factor (KLF 10) expression in a sample comprising the peripheral blood cells;
   comparing the level of KLF10 in the sample to a reference level of KLF 10;
   identifying a subject who has a level of KLF 10 in the sample below the reference level as having PAD; and
   administering a treatment for PAD to the identified subject who has a level of KLF10 in the sample that is below the reference level, wherein the treatment comprises a lipid-lowering agent.

2. A method of diagnosing and treating diabetic vasculopathy in a subject with diabetes, the method comprising:
   isolating $CD34^+/VEGFR2^+$ pro-angiogenic peripheral blood cells from the subject by flow cytometry;
   performing an assay to determine a level of Krüppel-like Factor (KLF10) expression in a sample comprising the peripheral blood cells;
   comparing the level of KLF10 in the sample to a reference level of KLF10;
   identifying a subject who has a level of KLF10 in the sample below the reference level as having diabetic vasculopathy; and
   administering a treatment for diabetic vasculopathy to the identified subject who has a level of KLF10 in the sample that is below the reference level, wherein the treatment comprises an angiotensin-converting enzyme (ACE) inhibitor.

3. The method of claim 2, wherein the subject has type 2 diabetes.

4. The method of claim 1, further comprising
   performing an assay to determine a level of KLF10 expression in a subsequent sample comprising $CD34^+/VEGFR2^+$ pro-angiogenic peripheral blood cells from the subject; and
   comparing the level of KLF10 in the subsequent sample to the level of KLF10 in the earlier sample;
   wherein an increase in a level of KLF10 in the subsequent sample as compared to the earlier sample indicates that the treatment is effective.

5. The method of claim 2, further comprising
   performing an assay to determine a level of KLF10 expression in a subsequent sample comprising $CD34^+/VEGFR2^+$ pro-angiogenic peripheral blood cells from the subject; and
   comparing the level of KLF10 in the subsequent sample to the level of KLF10 in the earlier sample;
   wherein an increase in a level of KLF10 in the subsequent sample as compared to the earlier sample indicates that the treatment is effective.

6. The method of claim 1, wherein the level of KLF10 expression in the sample is determined by quantitative PCR, flow cytometry, or quantitative immunoassay.

7. The method of claim 2, wherein the level of KLF10 expression in the sample is determined by quantitative PCR, flow cytometry, or quantitative immunoassay.

8. A method of diagnosing and treating stent thrombosis in a subject with a stent, the method comprising:
   isolating $CD34^+/VEGFR2^+$ pro-angiogenic peripheral blood cells from the subject by flow cytometry;
   performing an assay to determine a level of Krüppel-like Factor (KLF10) expression in a sample comprising the peripheral blood cells;
   comparing the level of KLF10 in the sample to a reference level of KLF10;
   identifying a subject who has a level of KLF10 in the sample below the reference level as having stent thrombosis; and
   administering a treatment for stent thrombosis to the identified subject who has a level of KLF10 in the sample that is below the reference level, wherein the treatment comprises dual anti-platelet therapy.

9. The method of claim 8, further comprising
   performing an assay to determine a level of KLF10 expression in a subsequent sample comprising $CD34^+/VEGFR2^+$ pro-angiogenic peripheral blood cells from the subject; and
   comparing the level of KLF10 in the subsequent sample to the level of KLF10 in the earlier sample;
   wherein an increase in a level of KLF10 in the subsequent sample as compared to the earlier sample indicates that the treatment is effective.

10. The method of claim 8, wherein the level of KLF10 expression in the sample is determined by quantitative PCR, flow cytometry, or quantitative immunoassay.

11. The method of claim 1, wherein the lipid-lowering agent is a statin, fibrate, or niacin.

12. A method of diagnosing and treating stent thrombosis in a subject with a stent, the method comprising:
   isolating $CD34^+/VEGFR2^+$ pro-angiogenic peripheral blood cells from the subject by flow cytometry;

performing an assay to determine a level of Krüppel-like Factor (KLF10) expression in a sample comprising the peripheral blood cells;

comparing the level of KLF10 in the sample to a reference level of KLF10;

identifying a subject who has a level of KLF10 in the sample below the reference level as having stent thrombosis; and administering a treatment for stent thrombosis to the identified subject who has a level of KLF10 in the sample that is below the reference level, wherein the treatment comprises anti-coagulation therapy.

13. The method of claim 12, further comprising performing an assay to determine a level of KLF10 expression in a subsequent sample comprising $CD34^+$/ $VEGFR2^+$ pro-angiogenic peripheral blood cells from the subject; and comparing the level of KLF10 in the subsequent sample to the level of KLF10 in the earlier sample;

wherein an increase in a level of KLF10 in the subsequent sample as compared to the earlier sample indicates that the treatment is effective.

14. The method of claim 12, wherein the level of KLF10 expression in the sample is determined by quantitative PCR, flow cytometry, or quantitative immunoassay.

* * * * *

UNITED STATES PATENT AND TRADEMARK OFFICE
CERTIFICATE OF CORRECTION

PATENT NO. : 9,500,658 B2  
APPLICATION NO. : 14/003852  
DATED : November 22, 2016  
INVENTOR(S) : Mark W. Feinberg et al.

Page 1 of 1

It is certified that error appears in the above-identified patent and that said Letters Patent is hereby corrected as shown below:

On the Title Page

Column 2 (Other Publications), Line 23, delete "beta1" and insert -- beta1 --,

Column 2 (Other Publications), Line 27, delete "beta1" and insert -- beta1 --.

Signed and Sealed this  
Fourteenth Day of February, 2017

Michelle K. Lee  
*Director of the United States Patent and Trademark Office*